(12) United States Patent
Hiratake et al.

(10) Patent No.: US 10,774,098 B2
(45) Date of Patent: Sep. 15, 2020

(54) NAHLSGEN OPTICAL RESOLUTION METHOD

(71) Applicant: KYOTO UNIVERSITY, Kyoto-shi, Kyoto (JP)

(72) Inventors: Jun Hiratake, Kyoto (JP); Bunta Watanabe, Kyoto (JP); Ryuzo Yoshioka, Takatsuki (JP); Hideaki Ishida, Ube (JP)

(73) Assignees: KYOTO UNIVERSITY, Kyoto-shi, Kyoto (JP); NAHLS CORPORATION CO., LTD., Kyoto-shi, Kyoto (JP)

( * ) Notice: Subject to any disclaimer, the term of this patent is extended or adjusted under 35 U.S.C. 154(b) by 0 days.

(21) Appl. No.: 16/333,084

(22) PCT Filed: Sep. 12, 2017

(86) PCT No.: PCT/JP2017/032829
§ 371 (c)(1),
(2) Date: Mar. 13, 2019

(87) PCT Pub. No.: WO2018/051972
PCT Pub. Date: Mar. 22, 2018

(65) Prior Publication Data
US 2019/0225634 A1    Jul. 25, 2019

(30) Foreign Application Priority Data
Sep. 14, 2016   (JP) .................. 2016-179297

(51) Int. Cl.
| C07F 9/40 | (2006.01) |
| C07B 63/00 | (2006.01) |
| C07B 57/00 | (2006.01) |
| A61P 17/00 | (2006.01) |
| A61K 31/662 | (2006.01) |
| A61P 37/08 | (2006.01) |

(52) U.S. Cl.
CPC ............ C07F 9/4009 (2013.01); A61P 17/00 (2018.01); C07B 57/00 (2013.01); C07B 63/00 (2013.01); C07F 9/40 (2013.01); A61K 31/662 (2013.01); A61P 37/08 (2018.01); C07B 2200/07 (2013.01); Y02P 20/55 (2015.11)

(58) Field of Classification Search
CPC .......... C07F 9/4009; C07F 9/40; A61P 17/00; A61P 37/08; C07B 57/00; C07B 63/00; C07B 2200/07; Y02P 20/55; A61K 31/662
USPC ....................................................... 558/146
See application file for complete search history.

(56) References Cited

U.S. PATENT DOCUMENTS

2009/0163725 A1    6/2009   Hiratake et al.

FOREIGN PATENT DOCUMENTS

| JP | 2010-270115 A | 12/2010 |
| WO | 2007/066705 A1 | 6/2007 |

OTHER PUBLICATIONS

Simon S. Terzyan et al., "Human Gamma-Glutamyl Transpeptidase 1: Structures of the Free Enzyme, Inhibitor-Bound Tetrahedral Transistion States and Glutamate-Bound Enzyme Reveal Novel Movement within the Active Site during Catalysis", J. Biol. Chem., May 26, 2015, 23 pages.
Liyon Han et al., "Design, Synthesis, and Evaluation of γ-Phosphono Diester Analogues of Glutamate as Highly Potent Inhibitors and Active Site Probes of γ-Glutamyl Transpeptidase", Biochemistry, 2007, pp. 1432-1447, vol. 46, No. 5.
Akane Kamiyama et al., "Phosphonate-based irreversible inhibitors of human γ-glutamyl transpeptidase (GGT). GGsTop is a non-toxic and highly selective inhibitor with critical electrostatic interaction with an active-site residue Lys562 for enhanced inhibitory activity", Bioorganic & Medicinal Chemistry, 2016, pp. 5340-5352, vol. 24.
Bunta Watanabe et al., "An improved synthesis of the potent and selective γ-glutamyl transpeptidase inhibitor GGsTop together with an inhibitoiy activity evaluation of its potential hydrolysis products", Tetrahedron Letters, 2017, pp. 3700-3703, vol. 58.
International Search Report for PCT/JP2017/032829 dated Oct. 24, 2017, [PCT/ISA/210].
Extended European Search Report dated Mar. 27, 2020 from European Patent Office in EP Application No. 17850874.3.

*Primary Examiner* — Kristin A Vajda
(74) *Attorney, Agent, or Firm* — Sughrue Mion, PLLC

(57) ABSTRACT

Provided is a method for separating the four optical isomers of Nahlsgen. The method according to the present invention for producing a mixture of a D-2-amino-4-[(Rp)-(3-carboxymethylphenoxy)(methoxy)phosphoryl]butanoic acid hydrate and an L-2-amino-4-[(Sp)-(3-carboxymethylphenoxy)(methoxy)phosphoryl]butanoic acid hydrate includes subjecting a mixture of the four optical isomers, represented by Formula (1'), to fractional crystallization from water or from a solvent mixture of water and a water-soluble organic solvent, to precipitate a mixture of a compound represented by Formula (1-1'-1) and a compound represented by Formula (1-4'-1), where Formulae (1'), (1-1'-1), and (1-4'-1) are expressed as follows:

[Chem. 22]

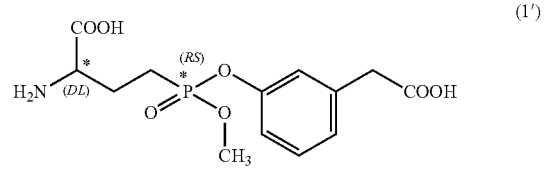

[Chem. 2]

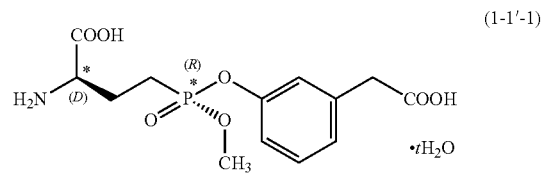

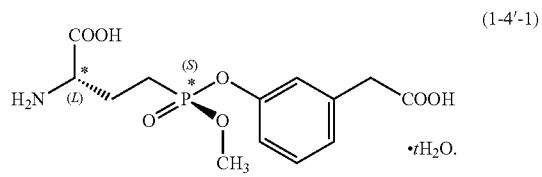

12 Claims, 5 Drawing Sheets

[FIG. 1]
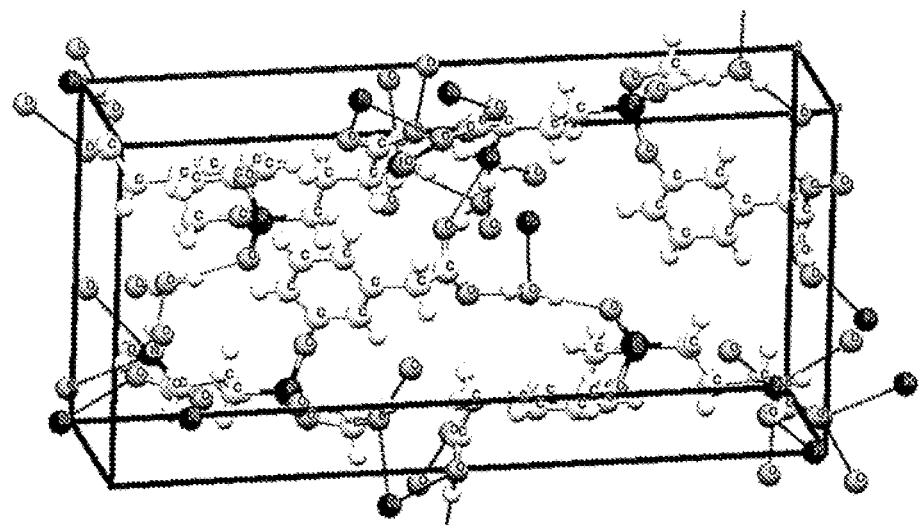
[FIG. 2]
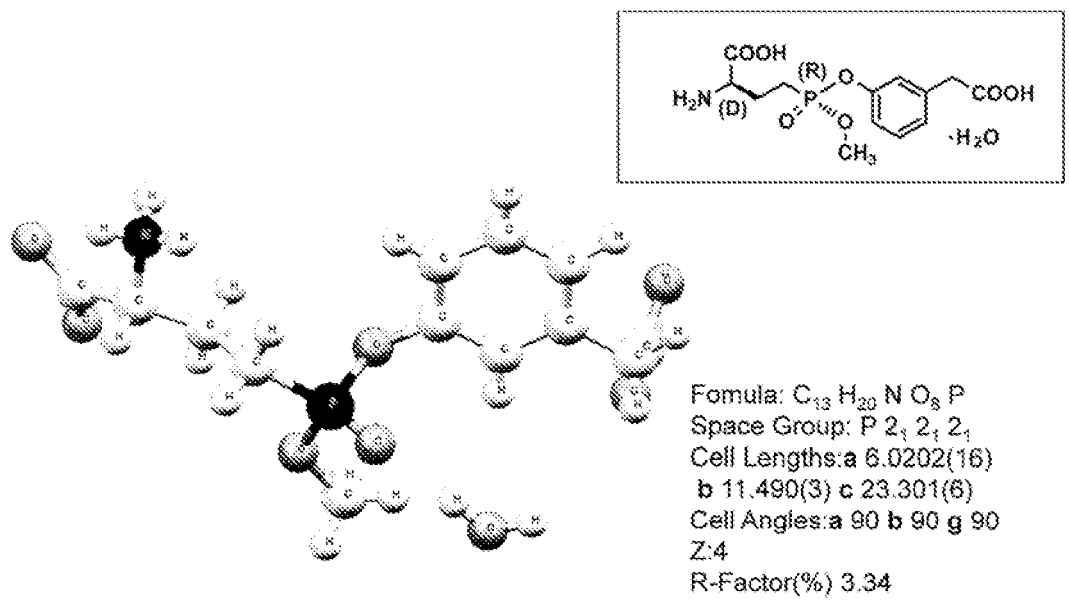

[FIG. 3]
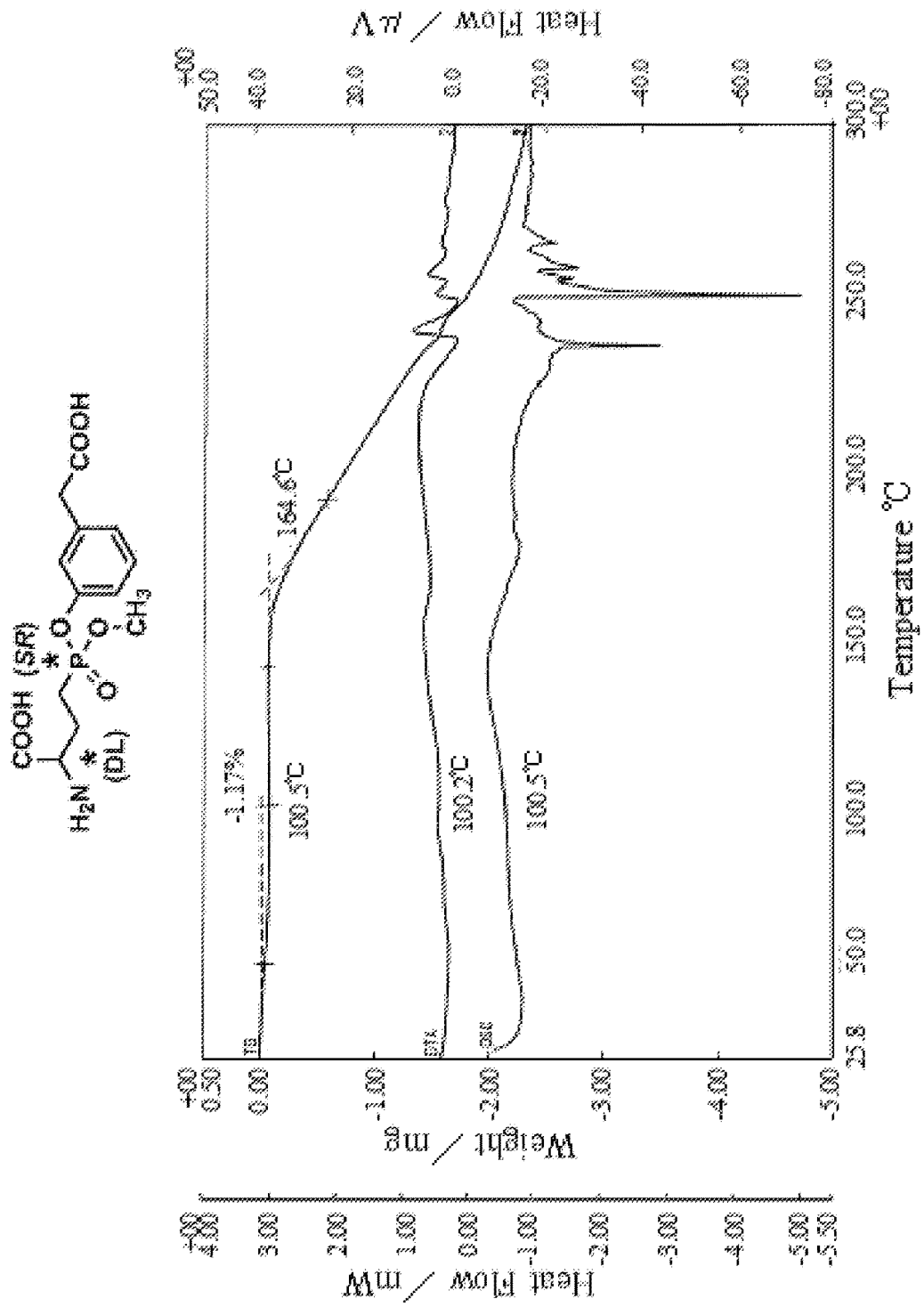

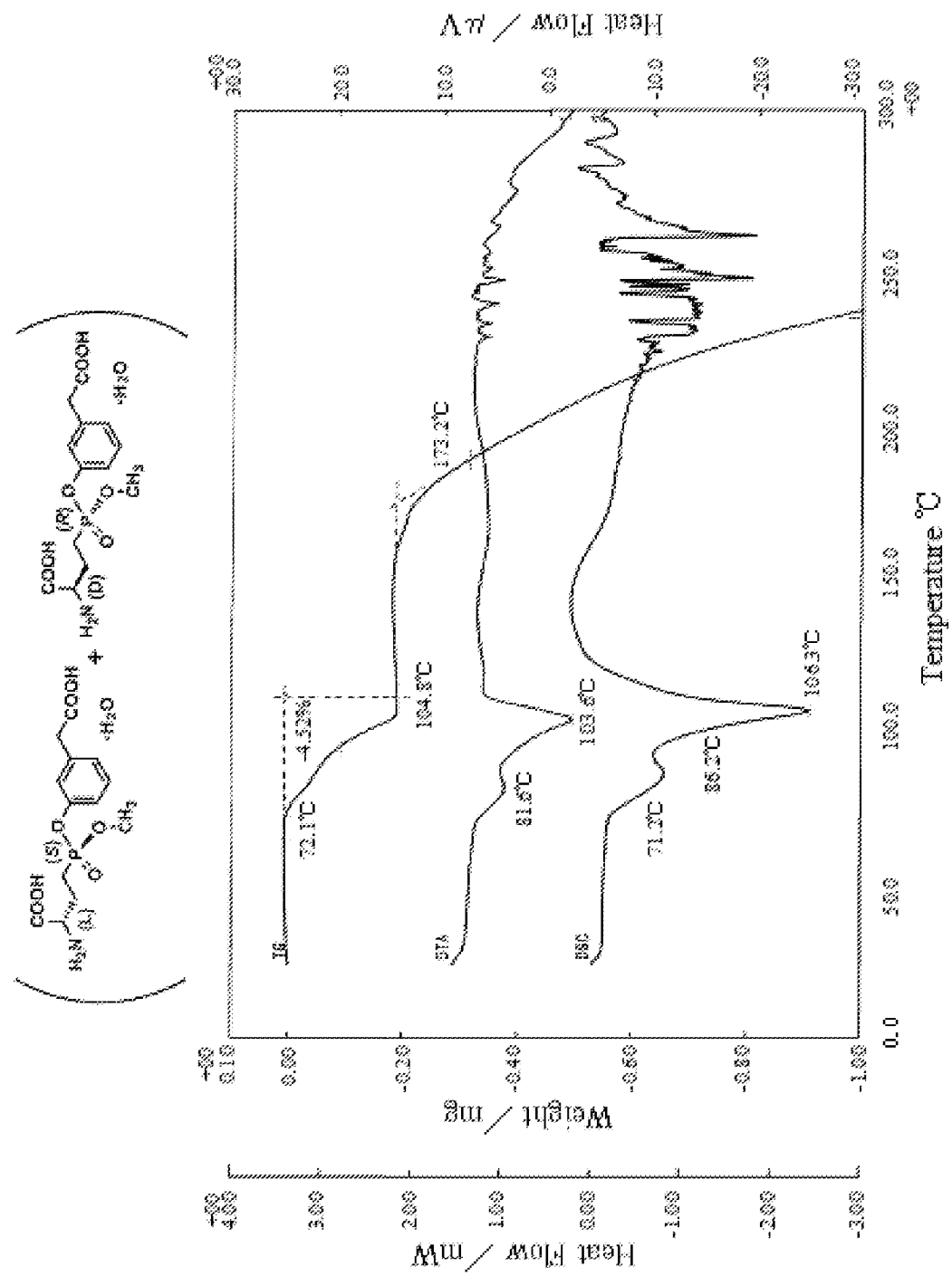
[FIG. 4]

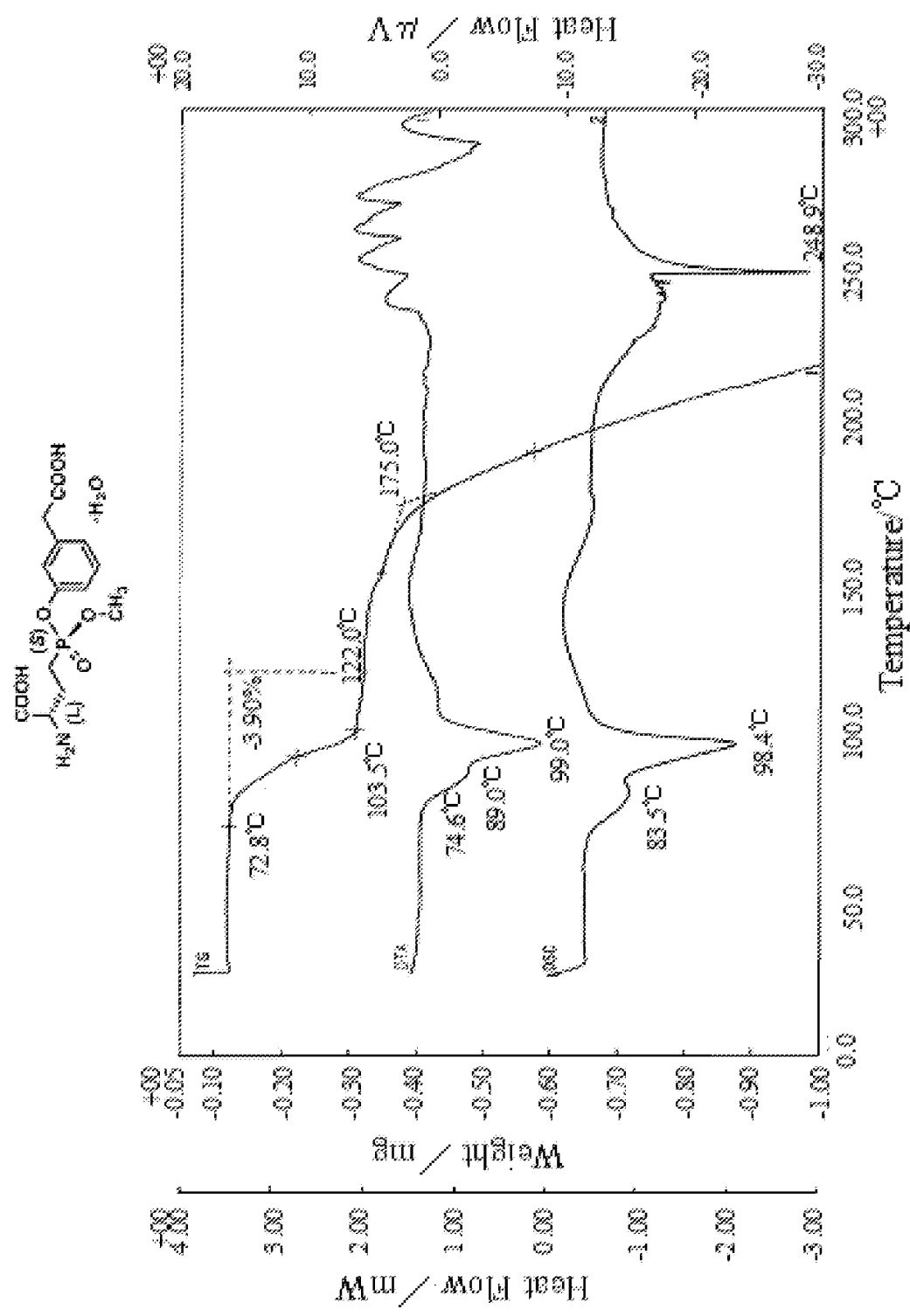
[FIG. 5]

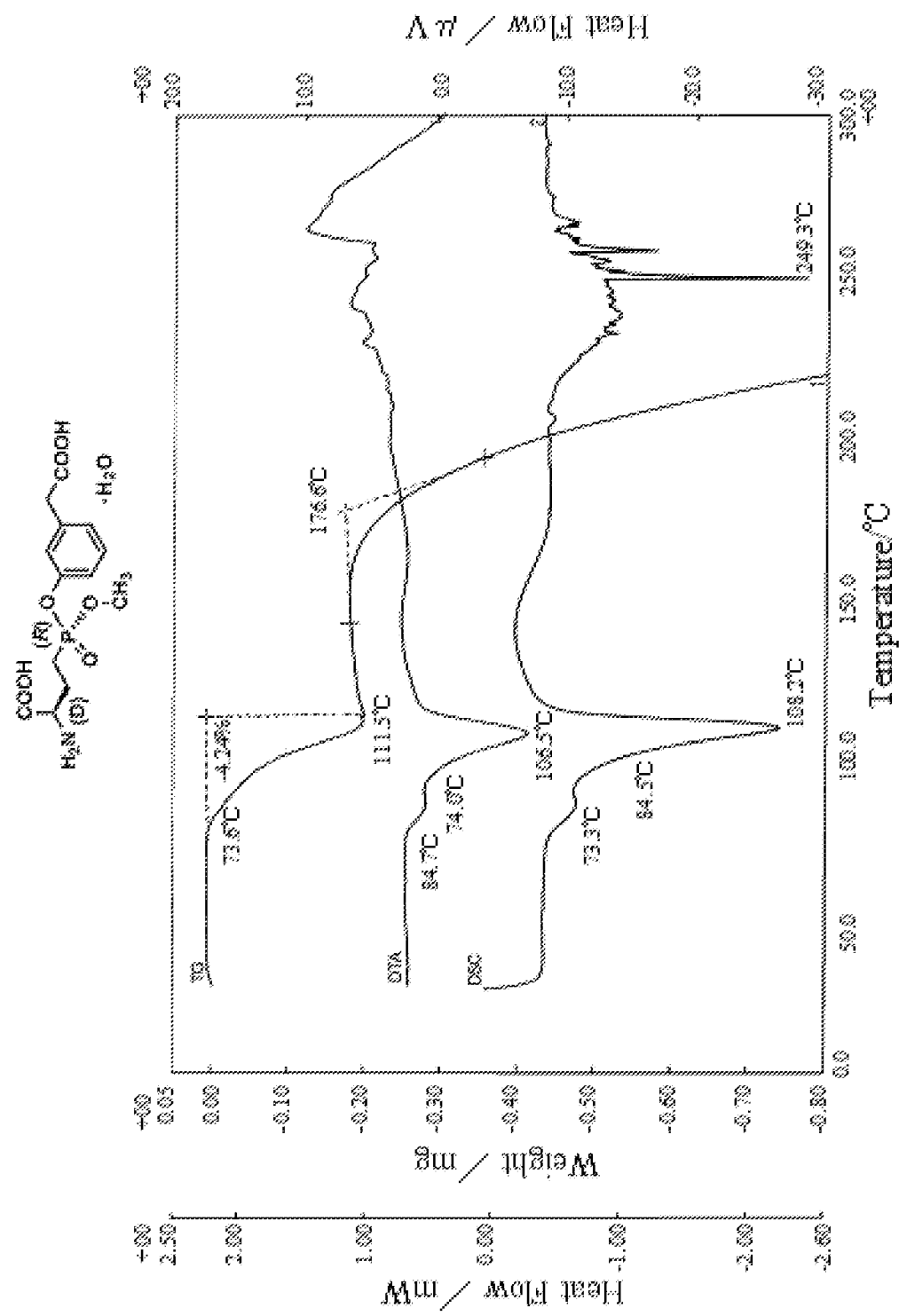
[FIG. 6]

NAHLSGEN OPTICAL RESOLUTION METHOD

CROSS REFERENCE TO RELATED APPLICATIONS

This application is a National Stage of International Application No. PCT/JP2017/032829 filed Sep. 12, 2017, claiming priority based on Japanese Patent Application No. 2016-179297 filed Sep. 14, 2016, the entire contents of which are incorporated herein by reference.

TECHNICAL FIELD

The present invention relates to a method for optically resolving Nahlsgen; and to optically active compounds which are isolated by the optical resolution method.

BACKGROUND ART

Nahlsgen (registered trademark) or GGsTop (generic name: DL-2-amino-4-[(RSp)-(3-carboxymethylphenoxy)(methoxy)phosphoryl]butanoic acid) is known as an excellent GGT inhibitor (for example, Patent Literature (PTL) 1).

Nahlsgen is a mixture of four optical isomers. However, there has not yet been known a method for completely separating the four optical isomers from the mixture. In addition, Nahlsgen at room temperature is not crystallized, but is in an oily state; and an amorphous powdery solid, which is finally obtained through lyophilization, is deliquescent and is liable to decompose at room temperature. The powdery solid therefore has to be stored in cold storage or frozen storage and is very hard to handle.

CITATION LIST

Patent Literature

PTL 1: Japanese Unexamined Patent Application Publication (JP-A) No. 2010-270115

SUMMARY OF INVENTION

Technical Problem

Accordingly, the present invention has an object to provide a method for approximately completely separating the four optical isomers constituting Nahlsgen.

The present invention has another object to provide a method for efficiently producing each of the four optical isomers constituting Nahlsgen, individually.

The present invention has still another object to individually provide the four optical isomers constituting Nahlsgen, and synthetic intermediates for the four optical isomers.

The present invention has yet another object to provide a novel compound that is derived from Nahlsgen, offers an excellent GGT inhibitory activity, and has excellent storage stability at room temperature.

Solution to Problem

After intensive investigations to achieve the objects, the inventors of the present invention found that two of the four optical isomers of Nahlsgen are crystallized as hydrates. The finding of the hydrate crystals led to successful single crystallization of them and led to identification of absolute configurations of all the four optical isomers of Nahlsgen by X-ray crystallography. The present invention has been made on the basis of these findings.

Specifically, the present invention provides a method for producing a mixture of a D-2-amino-4-[(Rp)-(3-carboxymethylphenoxy)(methoxy)phosphoryl]butanoic acid hydrate and an L-2-amino-4-[(Sp)-(3-carboxymethylphenoxy)(methoxy)phosphoryl]butanoic acid hydrate. The method includes subjecting a mixture of four optical isomers represented by Formulae (1-1') to (1-4') to fractional crystallization from water or from a solvent mixture of water and a water-soluble organic solvent, to give a mixture of a D-2-amino-4-[(Rp)-(3-carboxymethylphenoxy)(methoxy)phosphoryl]butanoic acid hydrate represented by Formula (1-1'-1) and an L-2-amino-4-[(Sp)-(3-carboxymethylphenoxy)(methoxy)phosphoryl]butanoic acid hydrate represented by Formula (1-4'-1), where Formulae (1-1'), (1-2'), (1-3'), (1-4') and Formulae (1-1'-1) and (1-4'-1) are expressed as follows:

[Chem. 1]

(1-1')

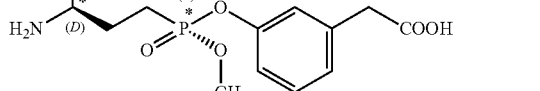

(1-2')

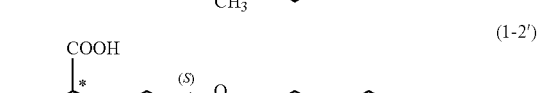

(1-3')

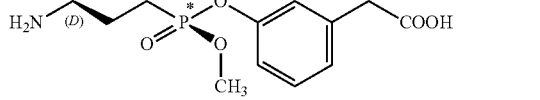

(1-4')

wherein the atoms marked with an asterisk (*) indicate asymmetric atoms,

[Chem. 2]

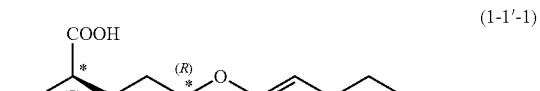

(1-1'-1)

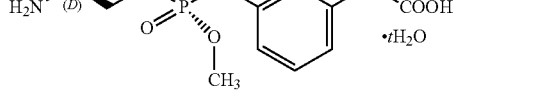

(1-4'-1)

wherein t represents a number greater than 0; and * is as defined above.

The present invention also provides a mixture of a D-2-amino-4-[(Rp)-(3-carboxymethylphenoxy)(methoxy)phosphoryl]butanoic acid hydrate represented by Formula (1-1'-1) and an L-2-amino-4-[(Sp)-(3-carboxymethylphenoxy)(methoxy)phosphoryl]butanoic acid hydrate represented by Formula (1-4'-1), where Formulae (1-1'-1) and (1-4'-1) are expressed as follows:

[Chem. 3]

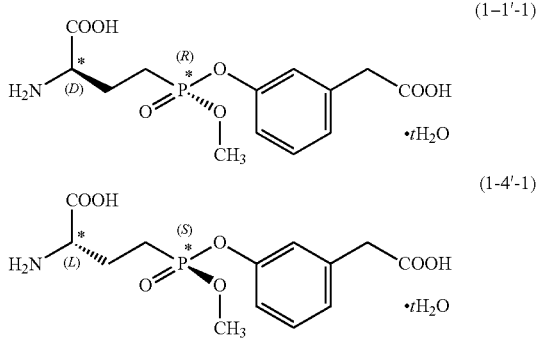

wherein the atoms marked with an asterisk (*) indicate asymmetric atoms; and t represents a number greater than 0.

The present invention also provides a D-2-amino-4-[(Rp)-(3-carboxymethylphenoxy)(methoxy)phosphoryl]butanoic acid hydrate represented by Formula (1-1'-1):

[Chem. 4]

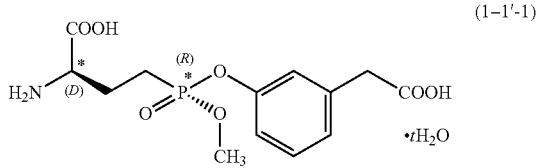

wherein the atoms marked with an asterisk (*) indicate asymmetric atoms; and t represents a number greater than 0.

The present invention also provides an L-2-amino-4-[(Sp)-(3-carboxymethylphenoxy)(methoxy)phosphoryl]butanoic acid hydrate represented by Formula (1-4'-1):

[Chem. 5]

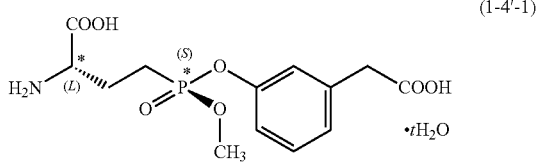

wherein the atoms marked with an asterisk (*) indicate asymmetric atoms; and t represents a number greater than 0.

The present invention also provides a method for producing a diastereomeric mixture of a D-2-amino-4-[(Rp)-(3-carboxymethylphenoxy) (methoxy)phosphoryl]butanoic acid derivative and a D-2-amino-4-[(Sp)-(3-carboxymethylphenoxy)(methoxy)phosphoryl]butanoic acid derivative. The method includes esterifying the phosphoric acid moiety of D-2-amino-4-phosphonobutanoic acid represented by Formula (2), to give a diastereomeric mixture, represented by Formula (2-1), of a D-2-amino-4-[(Rp)-(3-carboxymethylphenoxy)(methoxy)phosphoryl]butanoic acid derivative and a D-2-amino-4-[(Sp)-(3-carboxymethylphenoxy)(methoxy)phosphoryl]butanoic acid derivative, where Formulae (2) and (2-1) are expressed as follows:

[Chem. 6]

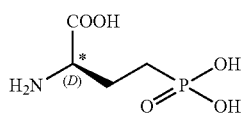

wherein the atoms marked with an asterisk (*) indicate asymmetric atoms,

[Chem. 7]

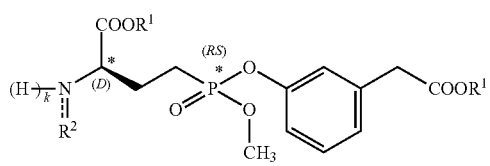

wherein $R^1$ is, identically or differently in each occurrence, selected from hydrogen and a carboxy-protecting group; $R^2$ is selected from benzyloxycarbonyl, phenylmethylidene, and diphenylmethylidene, each being optionally substituted; k represents 0 or 1, where when $R^2$ is optionally substituted benzyloxycarbonyl, k is 1 and the bond between the specifies nitrogen atom and $R^2$ is a single bond, and when $R^2$ is optionally substituted phenylmethylidene or optionally substituted diphenylmethylidene, k is 0 and the bond between the specified nitrogen atom and $R^2$ is a double bond; and * is as defined above.

The present invention also provides a diastereomeric mixture of a D-2-amino-4-[(Rp)-(3-carboxymethylphenoxy)(methoxy)phosphoryl]butanoic acid derivative and a D-2-amino-4-[(Sp)-(3-carboxymethylphenoxy)(methoxy)phosphoryl]butanoic acid derivative, where the diastereomeric mixture is represented by Formula (2-1):

[Chem. 8]

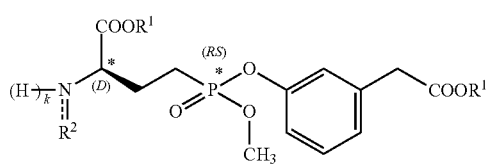

wherein $R^1$ is, identically or differently in each occurrence, selected from hydrogen and a carboxy protecting group; $R^2$ is selected from benzyloxycarbonyl, phenylmethylidene, and diphenylmethylidene, each being optionally substituted; k represents 0 or 1, where when $R^2$ is optionally substituted benzyloxycarbonyl, k is 1 and the bond between the specified nitrogen atom and $R^2$ is a single bond, and when $R^2$ is optionally substituted phenylmethylidene or optionally substituted diphenylmethylidene, k is 0 and the bond between the specified nitrogen atom and $R^2$ is a double bond; and the atoms marked with an asterisk (*) indicate asymmetric atoms.

The present invention also provides a method for optically resolving a diastereomeric mixture of a D-2-amino-4-[(Rp)-(3-carboxymethylphenoxy)(methoxy)phosphoryl]butanoic acid derivative and a D-2-amino-4-[(Sp)-(3-carboxymethylphenoxy)(methoxy)phosphoryl]butanoic acid derivative. The method includes subjecting a diastereomeric mixture, represented by Formula (2-1), of a D-2-amino-4-[(Rp)-(3-carboxymethylphenoxy)(methoxy)phosphoryl]butanoic acid derivative and a D-2-amino-4-[(Sp)-(3-carboxymethylphenoxy)(methoxy)phosphoryl]butanoic acid derivative to fractional crystallization to give one of optical isomers represented by Formula (1-1) and (1-2), where Formulae (2-1), (1-1), and (1-2) are expressed as follows:

[Chem. 9]

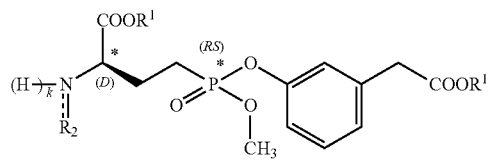

(2-1)

wherein $R^1$ is, identically or differently in each occurrence, selected from hydrogen and a carboxy-protecting group; $R^2$ is selected from benzyloxycarbonyl, phenylmethylidene, and diphenylmethylidene, each being optionally substituted; k represents 0 or 1, where when $R^2$ is optionally substituted benzyloxycarbonyl, k is 1 and the bond between the specified nitrogen atom and $R^2$ is a single bond, and when $R^2$ is optionally substituted phenylmethylidene or optionally substituted diphenylmethylidene, k is 0 and the bond between the specified nitrogen atom and $R^2$ is a double bond; and the atoms marked with an asterisk (*) indicate asymmetric atoms,

[Chem. 10]

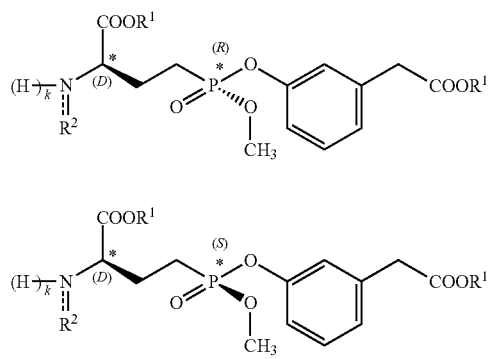

(1-1)

(1-2)

wherein $R^2$, k, and * are as defined above.

The present invention also provides a method for producing a D-2-amino-4-[(Rp)-(3-carboxymethylphenoxy)(methoxy)phosphoryl]butanoic acid hydrate. The method includes subjecting a D-2-amino-4-[(Rp)-(3-carboxymethylphenoxy)(methoxy)phosphoryl]butanoic acid derivative represented by Formulae (1-1) to deprotection treatment to give D-2-amino-4-[(Rp)-(3-carboxymethylphenoxy)(methoxy)phosphoryl]butanoic acid represented by Formula (1-1'), and subjecting the resulting D-2-amino-4-[(Rp)-(3-carboxymethylphenoxy)(methoxy)phosphoryl]butanoic acid to crystallization from water or from a solvent mixture of water and a water-soluble organic solvent, to give a D-2-amino-4-[(Rp)-(3-carboxymethylphenoxy)(methoxy)phosphoryl]butanoic acid hydrate represented by Formula (1-1'-1), where Formulae (1-1), (1-1'), and (1-1'-1) are expressed as follows:

[Chem. 11]

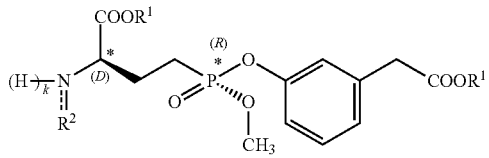

(1-1)

wherein $R^1$ is, identically or differently in each occurrence, selected from hydrogen and a carboxy-protecting group; $R^2$ is selected from benzyloxycarbonyl, phenylmethylidene, and diphenylmethylidene, each being optionally substituted; k represents 0 or 1, where when $R^2$ is optionally substituted benzyloxycarbonyl, k is 1 and the bond between the specified nitrogen atom and $R^2$ is a single bond, and when $R^2$ is optionally substituted phenylmethylidene or optionally substituted diphenylmethylidene, k is 0 and the bond between the specified nitrogen atom and $R^2$ is a double bond; and the atoms marked with an asterisk (*) indicate asymmetric atoms,

[Chem. 12]

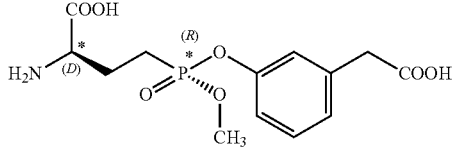

(1-1')

wherein * is as defined above,

[Chem. 13]

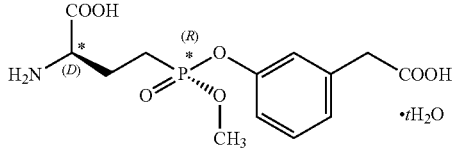

(1-1'-1)

wherein the atoms marked with an asterisk (*) indicate asymmetric atoms; and t represents a number greater than 0.

The present invention also provides a method for producing a diastereomeric mixture of an L-2-amino-4-[(Rp)-(3-carboxymethylphenoxy)(methoxy)phosphoryl]butanoic acid derivative and an L-2-amino-4-[(Sp)-(3-carboxymethylphenoxy) (methoxy)phosphoryl]butanoic acid derivative. The method includes esterifying the phosphoric acid moiety of L-2-amino-4-phosphonobutanoic acid represented by Formula (3), to give a diastereomeric mixture, represented by Formula (3-1), of an L-2-amino-4-[(Rp)-(3-carboxymethylphenoxy)(methoxy)phosphoryl]butanoic acid derivative and an L-2-amino-4-[(Sp)-(3-carboxymethylphenoxy) (methoxy)phosphoryl]butanoic acid derivative, where Formulae (3) and (3-1) are expressed as follows:

[Chem. 14]

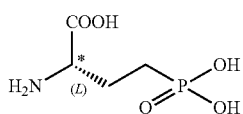

(3)

wherein the atom marked with an asterisk (*) indicates an asymmetric atom,

[Chem. 15]

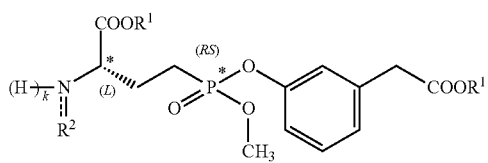

(3-1)

wherein $R^1$ is, identically or differently in each occurrence, selected from hydrogen and a carboxy-protecting group; $R^2$ is selected from benzyloxycarbonyl, phenylmethylidene, and diphenylmethylidene, each being optionally substituted; k represents 0 or 1, where when $R^2$ is optionally substituted benzyloxycarbonyl, k is 1 and the bond between the specified nitrogen atom and $R^2$ is a single bond, and when $R^2$ is optionally substituted phenylmethylidene or optionally substituted diphenylmethylidene, k is 0 and the bond between the specified nitrogen atom and $R^2$ is a double bond; and * is as defined above.

The present invention also provides a diastereomeric mixture of an L-2-amino-4-[(Rp)-(3-carboxymethylphenoxy)(methoxy)phosphoryl]butanoic acid derivative and an L-2-amino-4-[(Sp)-(3-carboxymethylphenoxy)(methoxy) phosphoryl]butanoic acid derivative, where the diastereomeric mixture is represented by Formula (3-1):

[Chem. 16]

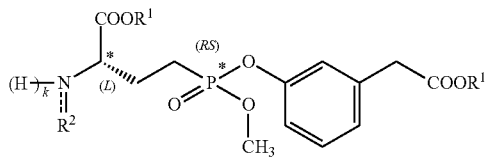

(3-1)

wherein $R^1$ is, identically or differently in each occurrence, selected from hydrogen and a carboxy-protecting group; $R^2$ is selected from benzyloxycarbonyl, phenylmethylidene, and diphenylmethylidene, each being optionally substituted; k represents 0 or 1, where when $R^2$ is optionally substituted benzyloxycarbonyl, k is 1 and the bond between the specified nitrogen atom and $R^2$ is a single bond, and when $R^2$ is optionally substituted phenylmethylidene or optionally substituted diphenylmethylidene, k is 0 and the bond between the specified nitrogen atom and $R^2$ is a double bond; and the atoms marked with an asterisk (*) indicate asymmetric atoms.

The present invention also provides a method for optically resolving a diastereomeric mixture of an L-2-amino-4-[(Rp)-(3-carboxymethylphenoxy)(methoxy)phosphoryl]butanoic acid derivative and an L-2-amino-4-[(Sp)-(3-carboxymethylphenoxy)(methoxy)phosphoryl]butanoic acid derivative. The method includes subjecting a diastereomeric mixture, represented by Formula (3-1), of an L-2-amino-4-[(Rp)-(3-carboxymethylphenoxy)(methoxy)phosphoryl]butanoic acid derivative and an L-2-amino-4-[(Sp)-(3-carboxymethylphenoxy)(methoxy)phosphoryl]butanoic acid derivative to fractional crystallization, to give one of optical isomers represented by Formula (1-3) and (1-4) where Formulae (3-1), (1-3), and (1-4) are expressed as follows:

[Chem. 17]

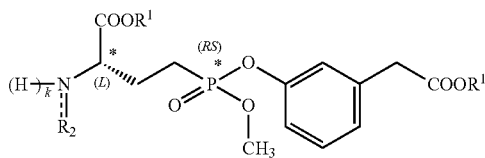

(3-1)

wherein $R^1$ is, identically or differently in each occurrence, selected from hydrogen and a carboxy-protecting group; $R^2$ is selected from benzyloxycarbonyl, phenylmethylidene, and diphenylmethylidene, each being optionally substituted; k represents 0 or 1, where when $R^2$ is optionally substituted benzyloxycarbonyl, k is 1 and the bond between the specified nitrogen atom and $R^2$ is a single bond, and when $R^2$ is optionally substituted phenylmethylidene or optionally substituted diphenylmethylidene, k is 0 and the bond between the specified nitrogen atom and $R^2$ is a double bond; and the atoms marked with an asterisk (*) indicate asymmetric atoms,

[Chem. 18]

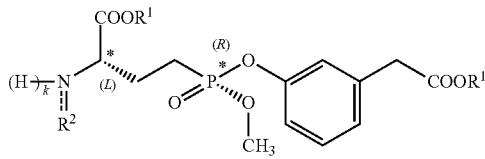

(1-3)

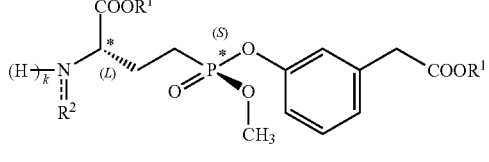

(1-4)

wherein $R^1$, $R^2$, k, and * are as defined above.

The present invention also provides a method for producing an L-2-amino-4-[(Sp)-(3-carboxymethylphenoxy)(methoxy)phosphoryl]butanoic acid hydrate. The method includes subjecting an L-2-amino-4-[(Sp)-(3-carboxymethylphenoxy)(methoxy)phosphoryl]butanoic acid derivative represented by Formula (1-4) to deprotection treatment to give L-2-amino-4-[(Sp)-(3-carboxymethylphenoxy)(methoxy)phosphoryl]butanoic acid represented by Formula (1-4'), and subjecting the L-2-amino-4-[(Sp)-(3-carboxymethylphenoxy)(methoxy)phosphoryl]butanoic acid to crystallization from water or from a solvent mixture of water and a water-soluble organic solvent, to give an L-2-amino-4-[(Sp)-(3-carboxymethylphenoxy)(methoxy)phosphoryl]butanoic acid hydrate represented by Formula (1-4'-1), where Formulae (1-4), (1-4'), and (1-4'-1) are expressed as follows:

[Chem. 19]

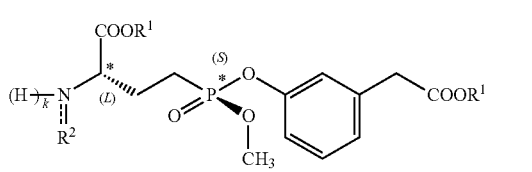

(1-4)

wherein R¹ is, identically or differently in each occurrence, selected from hydrogen and a carboxy-protecting group; R² is selected from benzyloxycarbonyl, phenylmethylidene, and diphenylmethylidene, each being optionally substituted; k represents 0 or 1, where when R is optionally substituted benzyloxycarbonyl, k is 1 and the bond between the specified nitrogen atom and R² is a single bond, and when R is optionally substituted phenylmethylidene or optionally substituted diphenylmethylidene, k is 0 and the bond between the specified nitrogen atom and R² is a double bond; and the atoms marked with an asterisk (*) indicate asymmetric atoms,

[Chem. 20]

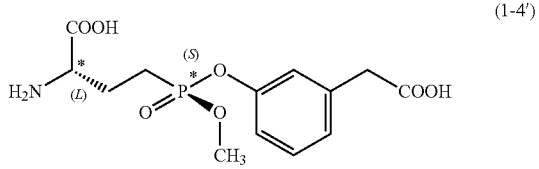

(1-4')

wherein * is as defined above,

[Chem. 21]

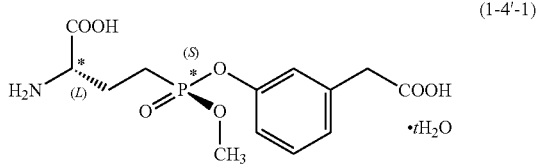

(1-4'-1)

wherein the atoms marked with an asterisk (*) indicate asymmetric atoms; and t represents a number greater than 0.

In this description, (D) and (L) are the configurations of ligands bonded to the asymmetric center carbon atom, where the configurations are indicated in D/L notation. (D) indicates that the amino group appears to the right, and (L) indicates that the amino group appears to the left, in a Fischer projection in which the carboxy is laid upward. (R) and (S) are the configurations of ligands bonded to the asymmetric center phosphorus atom, where the configurations are indicated in R/S notation.

Advantageous Effects of Invention

With the production method according to the present invention, a mixture of a D-2-amino-4-[(Rp)-(3-carboxymethylphenoxy)(methoxy)phosphoryl]butanoic acid hydrate and an L-2-amino-4-[(Sp)-(3-carboxymethylphenoxy)(methoxy)phosphoryl]butanoic acid hydrate, having a pharmacological activity equivalent to that of Nahlsgen, can be easily obtained as crystals from Nahlsgen without using a chiral column, where Nahlsgen is a mixture of four optical isomers.

The diastereomeric mixture production method according to the present invention using a chiral pool method gives a diastereomeric mixture, from which optical isomers can be easily isolated through fractional crystallization. The isolated optical isomers, when further subjected to deprotection treatment and fractional crystallization from water or from a solvent mixture of water and a water-soluble organic solvent, can give, individually a D-2-amino-4-[(Rp)-(3-carboxymethylphenoxy)(methoxy)phosphoryl]butanoic acid hydrate and an L-2-amino-4-[(Sp)-(3-carboxymethylphenoxy)(methoxy)phosphoryl]butanoic acid hydrate each with high purity.

The resulting D-2-amino-4-[(Rp)-(3-carboxymethylphenoxy)(methoxy)phosphoryl]butanoic acid hydrate, or L-2-amino-4-[(Sp)-(3-carboxymethylphenoxy)(methoxy)phosphoryl]butanoic acid hydrate, or mixture of them absorbs approximately no moisture at room temperature, has excellent storage stability, and is therefore easy to handle. These substances do not have cytotoxicity and are highly safe. In addition, these substances have excellent GGT inhibitory activities, and are therefore advantageously applicable to various GGT-involved diseases for therapeutic and/or prophylactic purpose.

BRIEF DESCRIPTION OF DRAWINGS

FIG. 1 is a schematic view of a packing structure of D-2-amino-4-[(Rp)-(3-carboxymethylphenoxy)(methoxy)phosphoryl]butanoic acid monohydrate;

FIG. 2 depicts X-ray crystallographical data for D-2-amino-4-[(Rp)-(3-carboxymethylphenoxy)(methoxy)phosphoryl]butanoic acid monohydrate;

FIG. 3 depicts thermal analysis results for Nahlsgen;

FIG. 4 depicts thermal analysis results for a mixture of D-2-amino-4-[(Rp)-(3-carboxymethylphenoxy)(methoxy)phosphoryl]butanoic acid monohydrate and L-2-amino-4-[(Sp)-(3-carboxymethylphenoxy)(methoxy)phosphoryl]butanoic acid monohydrate;

FIG. 5 depicts thermal analysis results for L-2-amino-4-[(Sp)-(3-carboxymethylphenoxy)(methoxy)phosphoryl]butanoic acid monohydrate; and FIG. 6 depicts thermal analysis results for D-2-amino-4-[(Rp)-(3-carboxymethylphenoxy)(methoxy)phosphoryl]butanoic acid monohydrate.

DESCRIPTION OF EMBODIMENTS

Diastereomeric Mixture Production Method

The diastereomeric mixture production method according to an embodiment of the present invention includes subjecting DL-2-amino-4-[(RSp)-(3-carboxymethylphenoxy)(methoxy)phosphoryl]butanoic acid represented by Formula (1') (hereinafter also referred to as "DL-GGsTop(RS)") to fractional crystallization from water or from a solvent mixture of water and a water-soluble organic solvent, to precipitate or deposit a mixture (preferably, an equal amount mixture) of a D-2-amino-4-[(Rp)-(3-carboxymethylphenoxy) (methoxy)phosphoryl]butanoic acid hydrate represented by Formula (1-1'-1) (hereinafter also referred to as a "D-GGsTop(R) hydrate") and an L-2-amino-4-[(Sp)-(3-carboxymethylphenoxy)(methoxy)phosphoryl]butanoic acid hydrate represented by Formula (1-4'-1) (hereinafter also referred to as an "L-GGsTop(S) hydrate"). Formula (1') is expressed as follows:

[Chem. 22]

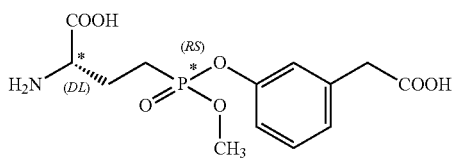

(1')

wherein the atoms marked with an asterisk (*) indicate asymmetric atoms. The DL-2-amino-4-[(RSp)-(3-carboxymethylphenoxy)(methoxy)phosphoryl]butanoic acid represented by Formula (1') is a mixture of four optical isomers, namely, D-2-amino-4-[(Rp)-(3-carboxymethylphenoxy)(methoxy)phosphoryl]butanoic acid represented by Formula (1-1') (hereinafter also referred to as "D-GGsTop (R)"), D-2-amino-4-[(Sp)-(3-carboxymethylphenoxy)(methoxy)phosphoryl]butanoic acid represented by Formula (1-2') (hereinafter also referred to as "D-GGsTop(S)"), L-2-amino-4-[(Rp)-(3-carboxymethylphenoxy)(methoxy)phosphoryl]butanoic acid represented by Formula (1-3') (hereinafter also referred to as "L-GGsTop(R)"), and L-2-amino-4-[(Sp)-(3-carboxymethylphenoxy)(methoxy)phosphoryl] butanoic acid represented by Formula (1-4') (hereinafter also referred to as "L-GGsTop(S)". Formulae (1-1'), (1-2'), (1-3'), and (1-4') are expressed as follows:

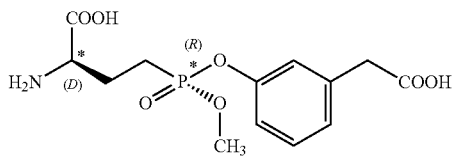

(1-1')

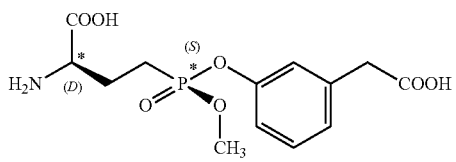

(1-2')

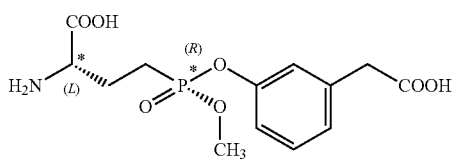

(1-3')

-continued

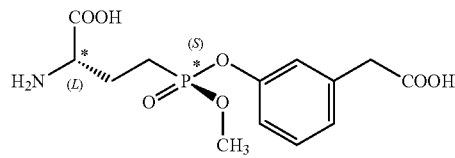

(1-4')

wherein the atoms marked with an asterisk (*) indicate asymmetric atoms. Formulae (1-1'-1) and (1-4'-1) are expressed as follows:

[Chem. 24]

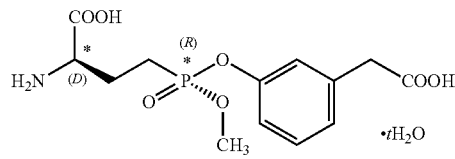

(1-1'-1)

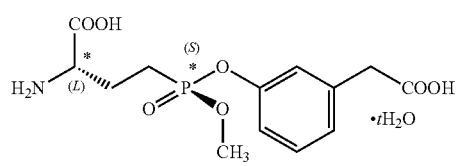

(1-4'-1)

In the formulae, t represents, independently is each occurrence, a number greater than 0 and is typically 0.5 to 5, preferably 0.5 to 3, and particularly preferably 1.

The water-soluble organic solvent is preferably selected from organic solvents that are dissolved in water in any proportion at room temperature (25° C.) and is preferably selected from those having solubility in water of 50% or more (particularly preferably 80% or more, and most preferably 95% or more).

Non-limiting examples of the water-soluble organic solvent include alcohols such as methanol, ethanol, propanol, isopropyl alcohol, t-butyl alcohol, and ethylene glycol; ethers such as 1,2-dimethoxyethane, tetrahydrofuran, and 1,4-dioxane; ketones such as acetone; and nitriles such as acetonitrile. Each of them may be used alone or in combination.

The water-soluble organic solvent for use herein is preferably selected from solvents having low solving power for the D-GGsTop (R) hydrate and L-GGsTop(S) hydrate, namely, poor solvents for them, and is particularly preferably selected from alcohols (and especially preferably selected from $C_1$-$C_5$ monohydric alcohols).

The water is preferably used in an amount of typically 1 to 100 parts by weight, more preferably 1 to 30 parts by weight, and particularly preferably 1 to 10 parts by weight, per 1 part by weight of DL-GGsTop(RS).

The solvent mixture contains water and the water-soluble organic solvent in such proportions that the amount of the water-soluble organic solvent is typically 1 to 10 parts by weight, and preferably 1 to 5 parts by weight, per 1 part by weight of water. Blending of the water-soluble organic solvent in water in a proportion within the range is effective to give better crystallization efficiency and is preferred.

DL-GGsTop (RS), when dissolved in water or the solvent mixture of water and a water-soluble organic solvent, is preferably stirred at an appropriate temperature (typically 0°

C. to 80° C., preferably 10° C. to 50° C., more preferably 15° C. to 40° C., and particularly preferably 15° C. to 35° C.)

The way to precipitate or separate the mixture may be selected typically from a technique of lowering the temperature, typically by cooling, of a solution resulting from dissolution of DL-GGsTop(S) in water or the solvent mixture of water and a water-soluble organic solvent (lowering the temperature down to typically 40° C. or lower (and preferably 20° C. or lower)); and a technique of concentrating the solution (this technique is advantageously usable when a water-soluble organic solvent having a higher boiling point as compared with water is used). The precipitation of the mixture is preferably performed with seeding of crystals of one or both of the D-GGsTop(R) hydrate and the L-GGsTop(S) hydrate. This is preferred for better crystallization efficiency.

The precipitated mixture can be recovered or collected by a well-known, common means such as centrifugal separation and/or filtration. The collected mixture may be subjected to a purification treatment such as filtration, concentration, distillation, extraction, crystallization, adsorption, or recrystallization, or any combination of them. In addition, the collected mixture may be subjected to a drying treatment (such as air drying, vacuum drying, or hot-air drying).

Diastereomeric Mixture Production Method (Chiral Pool Method)

The diastereomeric mixture production method according to an embodiment of the present invention is a method for producing a diastereomeric mixture (a mixture of a pair of compounds in a diastereomeric relationship with each other) through a so-called chiral pool method, by esterifying the phosphoric acid moiety of a starting material compound selected from D-2-amino-4-phosphonobutanoic acid represented by Formula (2) and L-2-amino-4-phosphonobutanoic acid represented by Formula (3). D-2-Amino-4-phosphonobutanoic acid represented by Formula (2), when used as the starting material, gives a diastereomeric mixture of a D-GGsTop(R) derivative and a D-GGsTop(S) derivative, represented by Formula (2-1). L-2-Amino-4-phosphonobutanoic acid represented by Formula (3), when used as the starting material, gives a diastereomeric mixture of an L-GGsTop(R) derivative and an L-GGsTop(S) derivative, represented by Formula (3-1):

[Chem. 25]

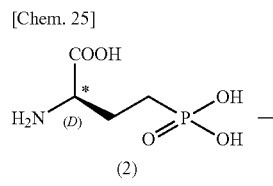

(2)

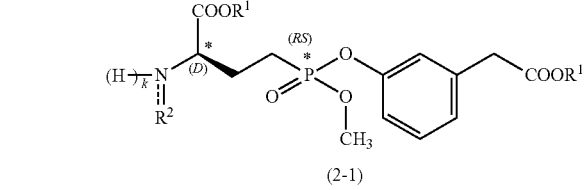

(2-1)

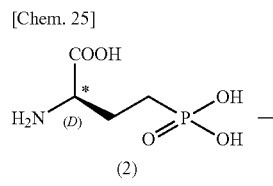

(3)

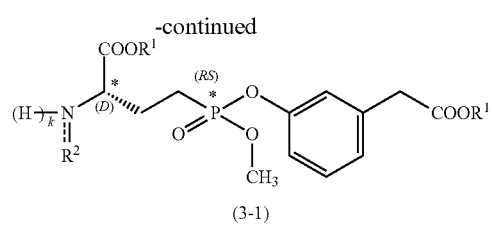

(3-1)

In the formulae, $R^1$ is, identically or differently in each occurrence, selected from hydrogen and a carboxy-protecting group; $R^2$ is selected from benzyloxycarbonyl, phenylmethylidene, and diphenylmethylidene, each being optionally substituted; k represents 0 or 1, where when $R^2$ is optionally substituted benzyloxycarbonyl, k is 1 and the bond between the specified nitrogen atom and $R^2$ is a single bond, and when $R^2$ is optionally substituted phenylmethylidene or optionally substituted diphenylmethylidene, k is 0 and the bond between the specified nitrogen atom and $R^2$ is a double bond; and the atoms marked with an asterisk (*) indicate asymmetric atoms.

The carboxy-protecting group as $R^1$ can be selected from protecting groups generally used in the field of organic synthesis and, in particular, is preferably selected from ester-forming protecting groups, which are groups that form an ester with the carboxy. Non-limiting examples of the protecting group include $C_1$-$C_5$ linear or branched chain alkyls (such as ethyl and t-butyl), $C_2$-$C_5$ linear or branched chain alkenyls (such as allyl), $C_6$-$C_{10}$ aryls (such as phenyl), and groups each including two or more of them being bonded through a single bond or a linkage group (such as carbonyl (—CO—) or ether bond (—O—)), where each of these groups may be substituted.

Specific, but non-limiting examples of the carboxy-protecting group include benzyl, benzyloxymethyl, phenacyl, triphenylmethyl, and diphenylmethyl. To the benzene ring constituting the carboxy-protecting group, one or more substituents may be bonded, where non-limiting examples of the substituents include halogens, $C_1$-$C_3$ alkoxys, and nitro.

Among them, a preferred, but non-limiting example of the carboxy-protecting group is optionally substituted benzyl, because such optionally substituted benzyl can be efficiently removed (deprotected) by catalytic hydrogen reduction or a hydrogen transfer reaction (hydride transfer reaction) typically using formic acid as a hydrogen source, where $R^1$ can be removed together with (or simultaneously with) $R^2$ in the catalytic hydrogen reduction, and can be removed alone in the hydrogen transfer reaction.

The group $R^2$ is an amino-protecting group and is selected from benzyloxycarbonyl, phenylmethylidene, and diphenylmethylidene, each of which may have one or more substituents such as halogens, $C_1$-$C_3$ alkoxys, and nitro. These protecting groups may be easily removed by catalytic hydrogen reduction.

Among them, the group $R^2$ is preferably optionally substituted benzyloxycarbonyl.

The reaction using D-2-amino-4-phosphonobutanoic acid represented by Formula (2) as the starting material to give a diastereomeric mixture of a D-GGsTop(R) derivative and a D-GGsTop(S) derivative, represented by Formula (2-1), is performed typically through the following steps. In the formulae below, $R^1$, $R^2$, k, and * are as defined above; and X represents, identically or differently in each occurrence, halogen (such as fluorine, chlorine, bromine, or iodine).

[Chem. 26]

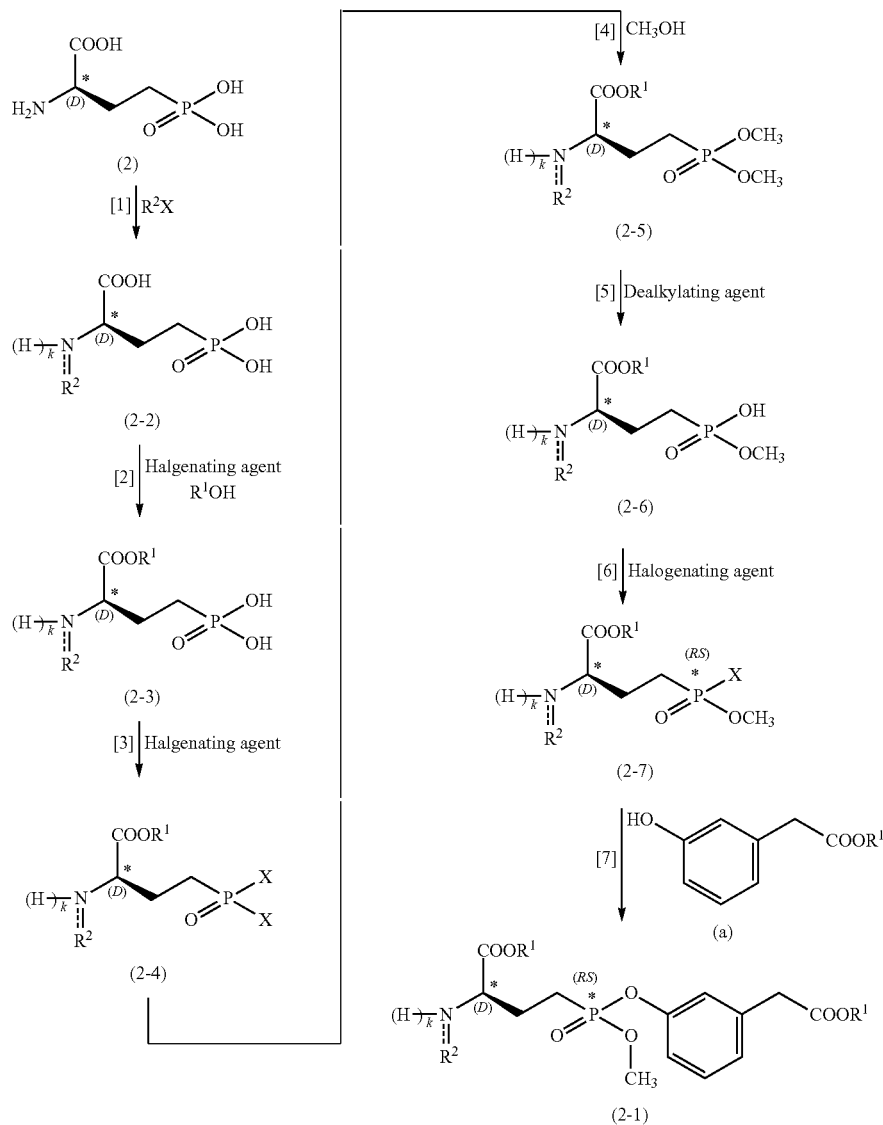

D-2-Amino-4-phosphonobutanoic acid represented by Formula (2) and L-2-amino-4-phosphonobutanoic acid represented by Formula (3), each for use as the starting material, can be produced typically by any of methods described in Non-Patent Literature (Kosolapoff G. M. Isomerization of Alkyl Phosphites. VII. Some Derivatives of 2-Bromoethane Phosphonic Acid J. Am. Chem. Soc. 1948, 70, 1971-1972; Chambers, J. R., Isbell, A. F. A new synthesis of amino phosphonic acids. J. Org. Chem. 1964, 29, 832-836.

Step [1] is the step of introducing a protecting group into the amino group of D-2-amino-4-phosphonobutanoic acid represented by Formula (2). For example, when $R^2$ is optionally substituted benzyloxycarbonyl, the protecting group can be introduced by reacting D-2-amino-4-phosphonobutanoic acid dissolved in a solvent with $R^2X$ (such as benzyl chloroformate or benzyl bromoformate), where necessary in the presence of a base (such as sodium hydroxide). When $R^2$ is optionally substituted phenylmethylidene or optionally substituted diphenylmethylidene, the protecting group can be introduced by reacting D-2-amino-4-phosphonobutanoic acid with optionally substituted benzaldehyde or optionally substituted benzophenone, where necessary in the presence of an acid catalyst.

Non-limiting examples of the solvent for use herein include water; halogenated hydrocarbon solvents; saturated or unsaturated hydrocarbon solvents; aromatic hydrocarbon solvents; and ether solvents, each of which may be used alone or in combination.

The reaction in Step [1] may be performed at a temperature of preferably around room temperature (15° C. to 25° C.), for a time of typically about 10 to about 40 hours.

Step [2] is the step of introducing a protecting group into the carboxy group of D-2-amino-4-phosphonobutanoic acid represented by Formula (2). This step may be performed by reacting a compound represented by Formula (2-2), resulting from Step [1], with a halogenating agent such as thionyl chloride to give a corresponding carboxylic halide, and reacting the carboxylic halide with $R^1OH$.

The reaction in Step [2] may be performed at a temperature of preferably 5° C. to 30° C., for a time of typically about 1 to about 10 hours.

Step [1] and Step [2] may be performed in reverse sequence. Namely, Step [2] and Step [1] may be performed is this sequence.

Step [3] is the step of reacting a compound represented by Formula (2-3), resulting through Steps [1] and [2], with a halogenating agent to substitute the hydroxys of the phosphonic acid moiety with halogens to thereby give a compound represented by Formula (2-4). A non-limiting example of the halogenating agent is oxalyl dichloride. Each of different halogenating agents may be used alone or in combination. The reaction is preferably performed in the presence of a catalyst (such as N,N-dimethylformamide), and a solvent (such as halogenated hydrocarbon solvents and ether solvents).

The reaction in Step [3] may be performed at a temperature of preferably 5° C. to 30° C., for a time of typically about 1 to about 10 hours.

Step [4] is the step of reacting a compound represented by Formula (2-4), resulting through Step [3], with methanol to substitute halogens in the phosphonic acid moiety with methoxys to thereby give a compound represented by Formula (2-5). This reaction is preferably performed in the presence of a base. Non-limiting examples of the base include triethylamine, tributylamine, diisopropylethylamine, N-methylpiperidine, N-methylmorpholine, die thylisopropylamine, N-methylimidazole, and pyridine. The reaction is preferably performed in the presence of a solvent. The solvent for use herein is preferably dichloromethane.

The reaction in Step [4] is performed at a temperature of preferably 5° C. to 30° C., for a time of typically about 1 to about 20 hours.

Step [5] is the step of reacting a compound represented by Formula (2-5), resulting through Step [4], with a dealkylating agent to remove one of the two methoxys in the phosphoric acid moiety to thereby give a compound represented by Formula (2-6). Non-limiting examples of the dealkylating agent include iodides of alkali metals or alkaline earth metals, such as sodium iodide, potassium iodide, and calcium iodide. Each of them may be used alone or in combination.

The reaction in Step [5] is preferably performed in the presence of a solvent (such as ketones exemplified by acetone and methyl ethyl ketone).

The reaction in Step [5] may be performed at a temperature of preferably 50° C. to 80° C., for a time of typically about 5 to about 10 hours.

Step [6] is the step of reacting a compound represented by Formula (2-6), resulting through Step [5], with a halogenating agent to substitute the hydroxy of the phosphonic acid moiety with halogen to thereby give a compound represented by Formula (2-7). This step is performed by a procedure similar to that for Step [3].

Step [7] is the step of reacting a compound represented by Formula (2-7), resulting through Step [6], with 2-(3-hydroxyphenyl)acetic acid or a derivative thereof (i.e., the compound represented by Formula (a)) to esterify the phosphonic acid moiety to thereby give a diastereomeric mixture of a D-GGsTop(R) derivative and a D-GGsTop(S) derivative, where the diastereomeric mixture is represented by Formula (2-1).

This reaction is preferably performed in the presence of a base. Non-limiting examples of the base include triethylamine, tributylamine, diisopropylethylamine, N-methylpiperidine, N-methylmorpholine, diethylisopropylamine, N-methylimidazole, and pyridine. Each of them may be used alone or in combination. The reaction is preferably performed in the presence of a solvent. The solvent for use herein is preferably dichloromethane.

The reaction in Step [7] may be performed at a temperature of preferably 5° C. to 30° C., for a time of typically about 1 to about 20 hours.

After the completion of each of Steps [1] to [7], the resulting reaction product may be purified, before a subsequent step, by a separation means such as filtration, concentrating, distillation, extraction, crystallization, adsorption, recrystallization, or column chromatography, or a separation means as any combination of them.

The diastereomeric mixture of an L-GGsTop(R) derivative and an L-GGTop(S) derivative, represented by Formula (3-1), can be produced by a procedure similar to that for the diastereomeric mixture of a D-GGsTop(R) derivative and a D-GGsTop(S) derivative, represented by Formula (2-1), except for using L-2-amino-4-phosphonobutanoic acid represented by Formula (3) as the starting material instead of D-2-amino-4-phosphonobutanoic acid represented by Formula (2).

Diastereomeric Mixture Optical Resolution Method

The method for optically resolving a diastereomeric mixture according to an embodiment of the present invention includes subjecting, to fractional crystallization, the diastereomeric mixture of a D-GGsTop(R) derivative and a D-GGsTop(S) derivative, represented by Formula (2-1), or the diastereomeric mixture of an L-GGsTop(R) derivative and an L-GGsTop(S) derivative, represented by Formula (3-1). This gives one of optical isomers represented by Formulae (1-1) and (1-2) when the diastereomeric mixture of a D-GGsTop(R) derivative and a D-GGsTop(S) derivative, represented by Formula (2-1), is used as the starting material; and gives one of optical isomers represented by Formulae (1-3) and (1-4) when the diastereomeric mixture of an L-GGsTop(R) derivative and an L-GGsTop(S) derivative, represented by Formula (3-1), is used as the starting material. Formulae (1-1), (1-2), (1-3), and (1-4) are expressed as follows:

[Chem. 27]

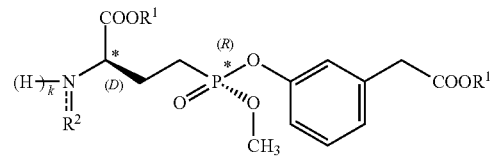

(1-1)

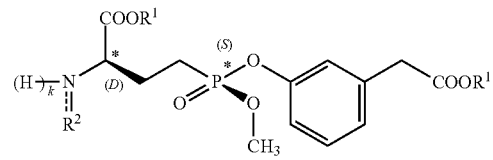

(1-2)

wherein $R^1$, $R^2$, k, and * are as defined above,

[Chem. 28]

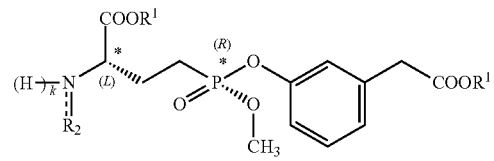

(1-3)

-continued

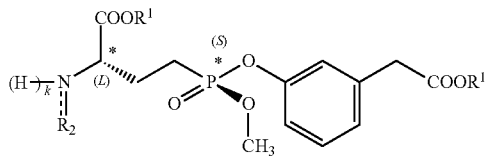

(1-4)

wherein $R^1$, $R^2$, k, and * are as defined above.

The fractional crystallization of the diastereomeric mixture can be performed by a well-known, common technique not limited, but is preferably performed typically by a technique in which the diastereomeric mixture is dissolved in a good solvent (such as methyl acetate, ethyl acetate, or butyl acetate), and a poor solvent (such as pentane, hexane, heptane, or octane) is added to the resulting solution. When the diastereomeric mixture of a D-GGsTop(R) derivative and a D-GGsTop(S) derivative, represented by Formula (2-1), is used as the starting material, it is preferred for better crystallization efficiency to seed one of the optical isomers represented by Formulae (1-1) and (1-2), which one is desired to be precipitated. When the diastereomeric mixture of an L-GGsTop(R) derivative and an L-GGsTop(S) derivative, represented by Formula (3-1), is used as the starting material, it is preferred for better crystallization efficiency to seed one of the optical isomers represented by Formulae (1-3) and (1-4), which one is desired to be precipitated.

The optical isomers represented by Formulae (1-1), (1-2), (1-3), and (1-4), which are obtained by the diastereomeric mixture optical resolution method, absorb approximately no moisture at room temperature, have excellent storage stability, and are therefore easy to handle. The optical isomers, when subjected to deprotection treatment, gives optical isomers represented respectively by Formulae (1-1'), (1-2'), (1-3'), and (1-4'). All of these compounds have approximately no cytotoxicity, are highly safe, and have excellent GGT inhibitory activities. These compounds are therefore used for various GGT-involved diseases exemplified by skin diseases such as allergic skin diseases, ichthyosis vulgaris, and senile xerosis, for therapeutic and/or prophylactic purpose. Accordingly, the optical isomers represented by Formulae (1-1), (1-2), (1-3), and (1-4) are useful as synthetic intermediates of the optical isomers represented by Formulae (1-1'), (1-2'), (1-3'), and (1-4').

D-GGsTop(R) Hydrate and L-GGsTop(S) Hydrate Production Method

The method according to an embodiment of the present invention for producing a D-GGsTop(R) hydrate and an L-GGsTop(S) hydrate includes subjecting a D-GGsTop(R) derivative to deprotection treatment to give D-GGsTop(R), and subjecting the resulting D-GGsTop(R) to crystallization from water or from a solvent mixture of water and a water-soluble organic solvent to give a D-GGsTop(R) hydrate; or subjecting an L-GGsTop(S) derivative to deprotection treatment to give L-GGsTop(S), and subjecting the resulting L-GGsTop(S) to crystallization from water or from a solvent mixture of water and a water-soluble organic solvent, to give an L-GGsTop(S) hydrate.

The crystallization of D-GGsTop(R) or L-GGsTop(S) from water or from a solvent mixture of water and a water-soluble organic solvent may be performed by a procedure in accordance with the procedure for the crystallization from water or from a solvent mixture of water and a water-soluble organic solvent in the diastereomeric mixture production method.

The deprotection treatment is not limited, as long as being such a treatment that can remove the amino-protecting group. When the carboxy group is protected, more specifically, when $R^1$ in Formulae (1-1) to (1-4) is a carboxy-protecting group, the deprotection treatment is not limited, as long as being such a treatment that can remove not only the amino-protecting group, but also the carboxy-protecting group. When both the amino group and the carboxy group are protected with protecting groups, the amino-protecting group and the carboxy-protecting group may be removed together (for example, removed in one step by the same method), or may be removed stepwise (for example, removed one by one by two different methods).

In particular in the present invention, it is preferred that the two different protecting groups (namely, the amino-protecting group and the carboxy-protecting group) are removed together (in one step) by the same method. For example, the two different protecting groups are preferably removed together by a reduction method (in particular, catalytic hydrogen reduction). This is preferred for enabling efficient deprotection.

The catalytic hydrogen reduction is generally performed by a procedure in which one of optical isomers, i.e., the D-GGsTop(R) derivative, the D-GGsTop(S) derivative, the L-GGsTop(R) derivative, and the L-GGsTop(S) derivative, is brought into contact with hydrogen gas in the presence of a catalyst. Non-limiting examples of the catalyst include Raney nickel, palladium-carbon (Pd—C), $PtO_2$, and Pd $(OH)_2$.

The deprotection treatment by the catalytic hydrogen reduction is preferably performed in the presence of a solvent. Non-limiting examples of the solvent include alcohols exemplified typically by $C_1$-$C_5$ monohydric aliphatic alcohols such as methanol, ethanol, and isopropanol; fatty acids exemplified typically by $C_1$-$C_5$ lower fatty acids such as formic acid, acetic acid, and propionic acid; and fatty acid esters exemplified typically by esters between a $C_1$-$C_5$ lower fatty acid and a $C_1$-$C_5$ monohydric alcohol, such as methyl acetate, ethyl acetate, and butyl acetate. Each of them may be used alone or in combination.

The deprotection treatment by the catalytic hydrogen reduction method is preferably performed by a procedure in which one of the optical isomers is reacted with the catalyst in a hydrogen gas atmosphere and in the presence of the solvent; or by a procedure in which hydrogen gas is bubbled into a mixture (solution) containing one of the optical isomers, the catalyst, and the solvent.

The deprotection treatment by the catalytic hydrogen reduction is performed at a temperature of typically about 0° C. to about 40° C., for a time of typically about 0.5 to about 5 hours. The deprotection treatment may be performed in any system such as batch system, semi-batch system, or continuous system.

The D-GGsTop(R) hydrate and the L-GGsTop(S) hydrate according to embodiments of the present invention have structures each including "t" water molecules being bonded and are thereby crystallized at room temperature. The packing structure illustrated in FIG. 1 demonstrates that the $H_2O$ molecules are significantly involved in the crystal structure.

The D-GGsTop(R) hydrate and the L-GGsTop(S) hydrate according to the present invention, and a mixture of them (hereinafter also referred to as "the hydrates and the hydrate mixture") absorb approximately no moisture at room temperature (namely, have approximately no deliquescency), have excellent storage stability, and are easy to handle. The hydrates and the hydrate mixture have approximately no cytotoxicity and are highly safe. In addition, the hydrates and the hydrate mixture have excellent GGT inhibitory activities. For example, the substances are capable of specifically acting upon skin fibroblasts to inhibit GGT, to cause decrease of glutathione, and to thereby enhance collagen production through anti-oxidative stress response. The substances are thereby capable of contributing to better barrier function to restrain entry of allergens and to restrain allergic reactions. In addition, the substances are capable of offering efficacies or effects typically of elastin production promotion, HSP47 production promotion, glutathione production promotion, fillagrin production promotion, fillagrin gene expression enhancement, and promotion of migration-growth of epidermal keratinocytes. The substances are therefore advantageously usable typically as GGT inhibitors, collagen production promoters, elastin production promoters, HSP47 production promoters, glutathione production promoters, fillagrin production promoters, fillagrin gene expression enhancers, and promoters for migration-growth of epidermal keratinocytes.

The hydrates and the hydrate mixture are advantageously usable for health and beauty purposes of the skin and hair. In addition the hydrates and the hydrate mixture are advantageously usable for various GGT-involved diseases for therapeutic and/or prophylactic purposes.

The hydrates and the hydrate mixture, when applied to epidermal tissues (such as skin, hair, and nails), are effective to promote or enhance collagen production and to give better barrier functions. In addition, the hydrates and the hydrate mixture, when applied to the skin, offer anti-aging effects and/or skin-whitening effects by promoting glutathione production and/or fillagrin production. The hydrates and the hydrate mixture are advantageously usable typically for treatment or prophylaxis of skin diseases or for skin care.

Non-limiting examples of the skin diseases include allergic skin diseases, ichthyosis vulgaris, and senile xerosis.

The hydrates and the hydrate mixture, when applied to the eyes, are effective for prevention or control of the development of the cataract, and for treatment or prophylaxis of the corneal ulcer, corneal epithelial abrasion, and keratitis. The hydrates and the hydrate mixture, when applied to the nose (specifically, typically to the nasal cavity or paranasal cavity), are effective typically to treat or prevent allergic rhinitis.

As demonstrated by the above description, the hydrates and the hydrate mixture are advantageously usable typically as dermatologic agents, ophthalmic preparations (eye drops), nasal drops, ear drops, preparations for oral use, cosmetics for skin care use, and additives such as bath additives.

The dermatologic agents include preparations for external application, such as creams, ointments, gels, lotions, liquid medicines, and tinctures; plasters or adhesive skin patches, such as cataplasms, plasters, tapes, and patches; and aerosolized agents (sprays). The preparations for oral use include gargle medicines and aerosolized medicines.

Non-limiting examples of the cosmetics for skis care use include makeup cosmetics such as foundation, eye shadow, mascara, eyebrow pencil or paint, cheek rouge, lipstick (rouge), and manicure; and basic skin care cosmetics such as lotions (face lotions), milky lotions, and beauty essence.

EXAMPLES

The present invention will be illustrated in further detail with reference to several examples below. It should be noted, however, that the examples are by no means intended to limit the scope of the present invention. In formulae below, Z represents benzyloxycarbonyl; and as represents benzyl.

Example 1

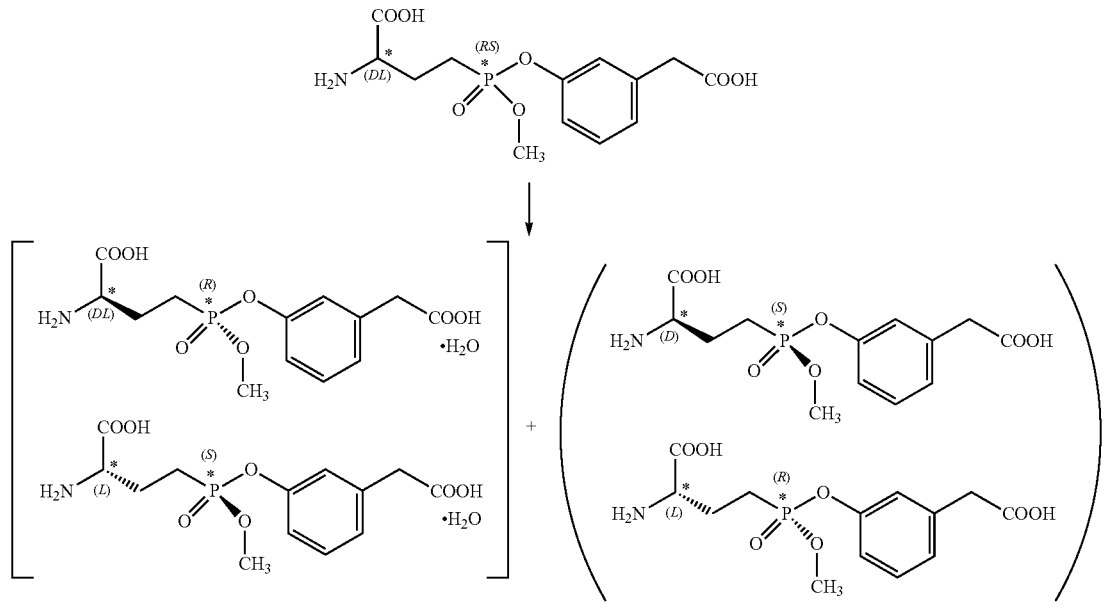

[Chem. 29]

DL-2-Amino-4-[(RSp)-(3-carboxymethylphenoxy)(methoxy)phosphoryl]butanoic acid (trade name GGsTop, supplied by Wako Pure Chemical Industries, Ltd., the thermal analysis results of which are given in FIG. 3) (10.0 g) was dissolved in water (10 mL) with heating at 70° C., and combined with ethanol (45 mL), seeded with a small amount of crystals of D-2-amino-4-[(Rp)-(3-carboxymethylphenoxy)(methoxy)phosphoryl]butanoic acid monohydrate/L-2-amino-4-[(Sp)-(3-carboxymethylphenoxy)(methoxy)phosphoryl]butanoic acid monohydrate at 40° C., followed by slow stirring at room temperature for 2 days. The mixture was further stirred at 15° C. for 3 hours to precipitate crystals, the precipitated crystals were filtered, washed, and dried, and yielded colorless crystals (3.86 g, in a yield of 39%). The resulting colorless crystals (3.80 g) were placed in water (3.8 mL) with heating at 70° C., and combined with and dissolved in methanol (3.8 mL) and ethanol (45 mL), followed by slow stirring at room temperature for 2 days. The mixture was further stirred at 15° C. for 3 hours to precipitate crystals, the precipitated crystals were filtered, washed, and dried, and yielded colorless crystals (3.10 g, in a yield of 82%). The colorless crystals (3.00 g) were recrystallized three times from a solvent mixture containing water (3.0 mL), methanol (6.0 mL), and ethanol (30 mL), and yielded, as colorless crystals, an equal-amount mixture (2.21 g, in a total yield of 24%) of D-2-amino-4-[(Rp)-(3-carboxymethylphenoxy)(methoxy)phosphoryl]butanoic acid monohydrate and L-2-amino-4-[(Sp)-(3-carboxymethylphenoxy)(methoxy)phosphoryl]butanoic acid monohydrate (the thermal analysis results of which are given in FIG. 4).

Mp (DSC): 106.3° C.,
$^1$H-NMR (600 MHz, D$_2$O) $\delta_H$: 2.12-2.34; (4H, m), 3.74; (2H, s), 3.87; (3H, d, J$_{H-P}$=11.3 Hz), 3.87-3.89; (1H, m), 7.16-7.17; (2H, m), 7.21; (1H, br d, J$_{H-H}$=7.9 Hz), 7.42; (1H, dd J$_{H-H}$=7.9 and 7.9 Hz).
$^{31}$P-NMR (121 MHz, D$_2$O) $\delta_P$: 32.5.
HRMS-FAB (m/z): [M-H$_2$O+H]$^+$ calcd for C$_{13}$H$_{19}$NO$_7$P, 332.0899; found, 332.0887.

Example 2

[Chem. 30]

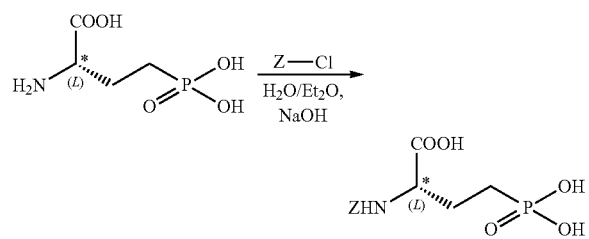

L-2-Amino-4-phosphonobutanoic acid (1.55 g, 8.47 mmol) was combined with water (5 mL) and diethyl ether (7 mL), ice-cooled, and combined with and dissolved in a solution of sodium hydroxide (1.05 g, 26.3 mmol) in water (10 mL), to give a solution. To the solution with vigorous stirring, benzyl chloroformate (3.25 g, 19.1 mmol) and sodium hydrogencarbonate (1.10 g, 13.1 mmol) were gradually added alternately. The resulting mixture was then vigorously stirred until the starting material disappeared. The disappearance of the starting material was checked through TLC (eluent: n-butanol/acetic acid/water=5/3/2 (v/v), coloring reagent: ninhydrin).

After being left stand, the reaction mixture was liquid-liquid separated, and the aqueous layer was washed with diethyl ether. The aqueous layer was combined with 6 N hydrochloric acid so as to have a pH of 1, and extracted with ethyl acetate.

The ethyl acetate layer was liquid-liquid separated, washed with saturated brine, and dried over anhydrous magnesium sulfate. The solvent was distilled off at 40° C. under reduced pressure, the residue was dried, and yielded colorless solid L-2-benzyloxycarbonylamino-4-phosphonobutanoic acid (2.64 g, in a yield of 98%).

[α]$_D^{25}$ +1.8 (c=1, MeOH)
IR (cm$^{-1}$): 3300-2000 (br), 3320, 2309, 1755, 1731, 1694, 1656, 1549, 1427, 1356, 1240, 1204, 1167, 1153, 1113, 1061, 1008, 944, 731, 693.

[Chem. 31]

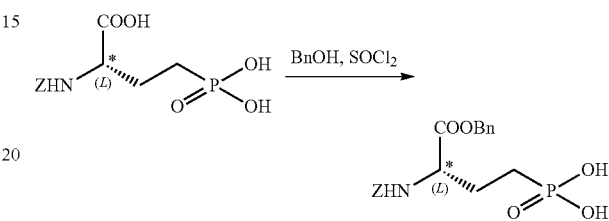

With ice-cooling, thionyl chloride (2.45 g, 20.6 mmol) was added dropwise to benzyl alcohol (27 mL), and the above-prepared L-2-benzyloxycarbonylamino-4-phosphonobutanoic acid (2.50 g 7.88 mmol) was added thereto while maintaining the mixture at 5° C. or lower. This reaction mixture was continuously stirred at room temperature until the starting material disappeared. The disappearance of the starting material was checked using TLC (eluent: n-butanol/methanol/water=5/3/2 (v/v), detection: UV).

After the reaction, excess benzyl alcohol was distilled off under reduced pressure, the residue was dissolved in ethyl acetate, and washed with saturated brine.

The ethyl acetate layer was liquid-liquid separated, dried over anhydrous magnesium sulfate, concentrated in vacuo at 40° C., the residue was combined with diethyl ether (25 mL), and stirred for one hour or longer. Precipitated crystals was filtered, dried in vacuo at 40° C., and thereby yielded colorless, powdery benzyl L-2-benzyloxycarbonylamino-4-phosphonobutanoate (2.87 g, in a yield of 89%).

[α]$_D^{25}$ −15.8 (c=1, MeOH)
IR (cm$^{-1}$) 3324, 3200-2500 (br), 3033, 2951, 2895, 1734, 1679, 1524, 1346, 1184, 1051, 997, 981, 940, 749, 696.

[Chem. 32]

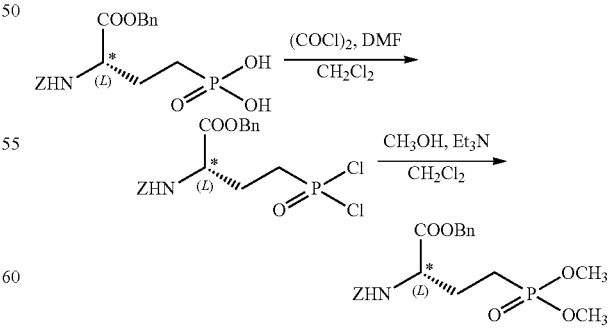

The prepared benzyl L-2-benzyloxycarbonylamino-4-phosphonobutanoate (2.70 g, 6.63 mmol) was suspended in dichloromethane (13 mL), combined with a catalytic amount of dimethylformamide, and combined with oxalyl dichloride (1.90 g, 15.0 mmol) added dropwise thereto. After being stirred at room temperature for a while, the reaction mixture was concentrated in vacuo, and yielded a brown oily substance. This was dissolved in dichloromethane (20 mL), combined with methanol (0.48 g, 15.0 mmol) under ice-cooling, and then combined with triethylamine (1.43 g, 14.1 mmol) added dropwise thereto. After the completion of dropwise addition, the mixture was stirred at room temperature overnight. The reaction mixture was combined with silica gel (6.6 g), concentrated in vacuo, and combined with ethyl acetate (40 mL), followed by thorough stirring. This was filtered, the filtrate was concentrated and dried in vacuo at 40° C., and yielded brown oily benzyl L-2-benzyloxycarbonylamino-4-(dimethoxyphosphoryl)butanoate (2.61 g, in a yield of 90%).

$[\alpha]_D^{25}$ −20.5 (c=1, MeOH), 99.9% ee (column: CHIRAL-PAK IB (5 μm, 4.6 mm in diameter by 250 mm); mobile phase: n-hexane/ethanol=95/5 (v/v); flow rate: 1.0 mL/min; temperature: 25° C.; detection wavelength: UV 220 nm)

IR (cm$^{-1}$): 3248, 3063, 3033, 2953, 2851, 1716, 1534, 1498, 1454, 1240, 1213, 1174, 1025, 816, 737, 696.

[Chem. 33]

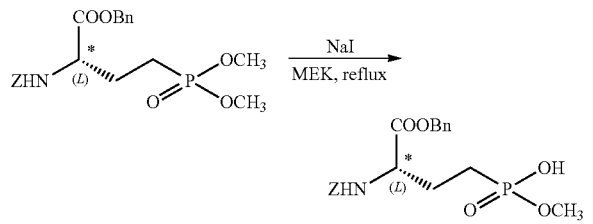

The prepared benzyl L-2-benzyloxycarbonylamino-4-(dimethoxyphosphoryl)butanoate (2.40 g, 5.51 mmol) was dissolved in methyl ethyl ketone (50 ml), combined with sodium iodide (1.32 g, 8.81 mmol), and refluxed for 4 hours. After checking that the starting material approximately disappeared using TLC (eluent: chloroform/methanol/acetic acid=85/15/3 (v/v), detection: UV), the reaction mixture was concentrated in vacuo, and combined with and dissolved in water (50 mL). This was combined with 6 N hydrochloric acid to be acidic, the precipitated yellowish-brown oily substance was extracted with dichloromethane, and dried over anhydrous magnesium sulfate. The resulting substance was concentrated and dried in vacuo at 40° C. to remove the solvent, and yielded brown oily benzyl L-2-benzyloxycarbonylamino-4 (hydroxymethoxyphosphoryl)butanoate (2.27 g, in a yield of 98%).

$[\alpha]_D^{25}$ −17.6 (c=1, MeOH)

IR (cm$^{-1}$): 3314, 3290, 3056, 3033, 2968, 2955, 2895, 1726, 1698, 1679, 1537, 1269, 1228, 1202, 1148, 1039, 965, 820, 753, 697.

[Chem. 34]

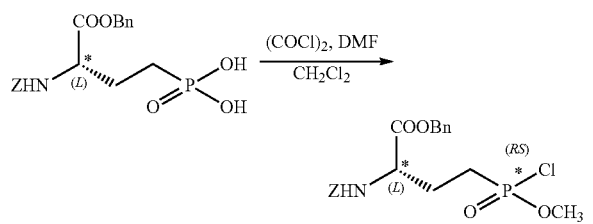

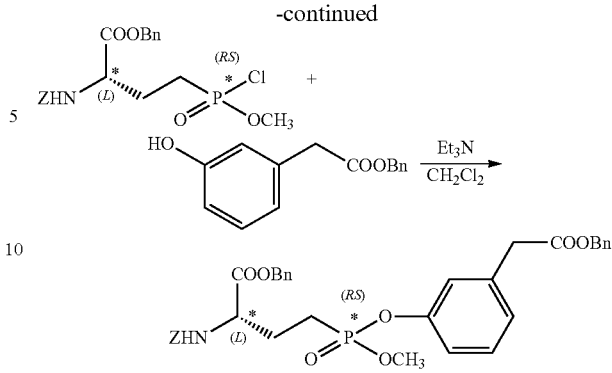

The prepared benzyl L-2-benzyloxycarbonylamino-4-(hydroxymethoxyphosphoryl)butanoate (2.22 g, 5.27 mmol) was dissolved in dichloromethane (20 mL), combined with a catalytic amount of dimethylformamide, combined with oxalyl dichloride (0.82 g, 6.46 mmol) added dropwise, and stirred at room temperature for 3 hours. The reaction mixture was concentrated in vacuo, the resulting brown oily substance was dissolved in dichloromethane (20 mL), combined with benzyl 3-hydroxyphenylacetate (1.29 g, 5.32 mmol), and cooled with ice. This was combined with triethylamine (0.66 g, 6.52 mmol) added dropwise and further stirred at room temperature overnight. The reaction mixture was concentrated in vacuo, the residue was subjected to silica gel column chromatography (hexane/ethyl acetate=4/1 to 1/2 (v/v)), and yielded yellow oily benzyl L-2-benzyloxycarbonylamino-4-[(RSp)-(3-benzyloxycarbonylmethylphenoxy)(methoxy)phosphoryl]butanoate (2.39 g, in a yield of 705).

$[\alpha]_D^{25}$ −10.8 (c=1, MeOH), 99.9% ee (column: CHIRAL-PAK IB (5 μm, 4.6 mm in diameter by 250 mm); mobile phase: n-hexane/ethanol=95/5 (v/v); flow rate: 1.0 mL/min; temperature: 30° C.; detection wavelength: UV 220 nm)

IR (cm$^{-1}$): 3269, 3063, 3033, 2953, 2852, 1953, 1868, 1721, 1239, 114.2, 1041, 1005, 972, 857, 736, 696.

[Chem. 35]

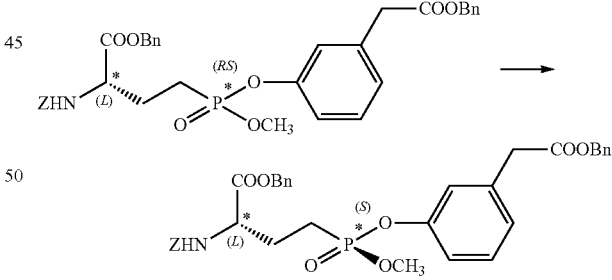

The prepared benzyl L-2-benzyloxycarbonylamino-4-[(RSp)-(3-benzyloxycarbonylmethylphenoxy)(methoxy)phosphoryl]butanoate (2.00 g) was dissolved in ethyl acetate (32 mL), to which heptane (62 mL) was gradually added. The resulting solution was seeded with a small amount of crystals of benzyl L-2-benzyloxycarbonylamino-4-[(Sp)-(3-benzyloxycarbonylmethylphenoxy)(methoxy)phosphoryl]butanoate, followed by stirring at room temperature for 2 hours. After being left stand in a refrigerator overnight, the mixture was further combined with heptane (10 mL), and stirred at room temperature for 3 hours. Thereafter this operation was repeated for 7 days, the resulting mixture was combined with heptane (16.5 mL in total), left stand in a refrigerator, and stirred at room temperature for 4 hours. Precipitated crystals were filtered, washed, dried at 40° C., and yielded benzyl L-2-benzyloxycarbonylamino-4-[(Sp)-(3-benzyloxycarbonylmethylphenoxy)(methoxy)phosphoryl]butanoate (0.51 g, in a yield of 26%).

$[\alpha]_D^{25}$ −16.7 (c=1, MeOH), 73.3% de (column: CHIRALPAK IB (5 μm, 4.6 mm in diameter by 250 mm); mobile phase: n-hexane/ethanol=95/5 (v/v); flow rate: 1.0 mL/min; temperature: 25° C.; detection wavelength: UV 220 nm)

The prepared benzyl L-2-benzyloxycarbonylamino-4-[(Sp)-(3-benzyloxycarbonylmethylphenoxy)(methoxy) phosphoryl]butanoate (0.49 g) was dissolved in ethyl acetate (16 mL), combined with heptane (43.3 mL) gradually added thereto, and stirred at room temperature for 4 hours. After being left stand in a refrigerator over two nights, the mixture was further combined with heptane (4.0 mL), and left stand in a refrigerator overnight. Precipitated crystals were filtered, washed, dried in vacuo at 40° C., and yielded benzyl L-2-benzyloxycarbonylamino-4-[(Sp)-(3-benzyloxycarbonylmethylphenoxy)(methoxy)phosphoryl]butanoate (0.35 g, in a yield of 71%).

$[\alpha]_D^{25}$ −18.8 (c=1, MeOH), 97.5% de (column: CHIRALPAK IB (5 μm, 4.6 mm in diameter by 250 mm); mobile phase: n-hexane/ethanol=95/5 (v/v); flow rate: 1.0 mL/min; temperature: 25° C.; detection wavelength: UV 220 nm)

IR (cm$^{-1}$): 3278, 3186, 3068, 3036, 2986, 2958, 2921, 2890, 2857, 1744, 1718, 1234, 1151, 1135, 1046, 990, 850, 751, 737, 697, 684.

[Chem. 36]

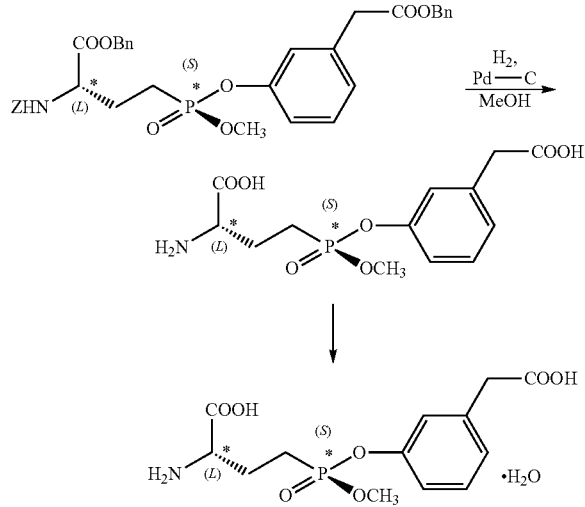

The prepared benzyl L-2-benzyloxycarbonylamino-4-[(Sp)-(3-benzyloxycarbonylmethylphenoxy)(methoxy) phosphoryl]butanoate (300 mg, 0.465 mmol) was dissolved in methanol (10 mL), combined with 10% palladium-carbon (22 mg) while purging the system with nitrogen gas, and the reaction mixture was then stirred at room temperature for 2 hours while blowing hydrogen gas thereinto. After the completion of the reaction, the palladium-carbon was filtered off using Celite, the filtrate was concentrated in vacuo, the residue was dissolved in water (10 ml), and washed with toluene (2.5 mL) three times. The aqueous solution was concentrated in vacuo, the residue was combined with ethanol (2.5 ml), and left stand in a refrigerator overnight. The mixture was subjected to sonication as appropriate, further left stand in a refrigerator overnight, precipitated crystals were filtered, washed, drilled in vacuo at 40° C., and yielded, as colorless crystals, L-2-amino-4-[(Sp)-(3-carboxymethylphenoxy)(methoxy)phosphoryl]butanoic acid monohydrate (134 mg, in a yield of 83%). The thermal analysis results of the resulting compound are given in FIG. 5.

Mp (DSC): 98.4° C., $[\alpha]_D^{25}$ −4.4 (c0.5, H$_2$O), 99.9% ee (column: OA-6100 (5 μm, 4.6 mm in diameter by 150 mm); mobile phase: 10% aqueous acetonitrile solution containing 2 mM copper sulfate; flow rate: 1.0 mL/min; temperature: 30° C.; detection wavelength: UV 254 nm)

IR (cm$^{-1}$): 3600-2300 (br), 1683, 1583, 1537, 1485, 1392, 1248, 1144, 1045, 982, 780.

Example 3

[Chem. 37]

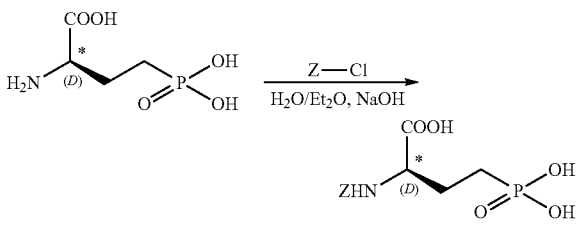

D-2-Amino-4-phosphonobutanoic acid (1.83 g, 10.0 mmol) was combined with water (10 mL) and diethyl ether (7.5 mL), ice-cooled, and combined with and dissolved in a solution of sodium hydroxide (1.20 g, 30.0 mmol) in water (10 mL). To the resulting solution with vigorous stirring, benzyl chloroformate (3.54 g, 20.8 mmol) and sodium hydrogencarbonate (1.36 g, 16.2 mmol) were added gradually, and the mixture was continuously stirred vigorously at room temperature until the starting material disappeared. The disappearance of the starting material was checked using TLC (eluent: chloroform/methanol/acetic acid=85/15/3 (v/v), coloring reagent: ninhydrin).

After being left stand, the reaction mixture was liquid-liquid separated, the aqueous layer was washed with diethyl ether, the resulting aqueous layer was combined with 6 N hydrochloric acid so as to have a pH of 1, and extracted with ethyl acetate.

The ethyl acetate layer was liquid-liquid separated, washed with saturated brine, dried over anhydrous magnesium sulfate, from which the solvent was distilled off at 40° C. under reduced pressure, the residue was dried, and yielded, as a colorless solid, D-2-(benzyloxycarbonyl) amino-4-phosphonobutanoic acid (2.92 g, in a yield of 92%).

$[\alpha]_D^{25}$ −2.0 (c=1, MeOH)

IR (cm$^{-1}$): 3300-2000 (br), 3318, 2286, 1754, 1730, 1694, 1654, 1548, 1428, 1356, 1240, 1205, 1168, 1153, 1113, 1062, 1008, 945, 732, 693.

[Chem. 38]

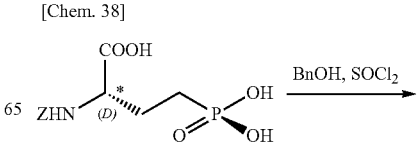

-continued

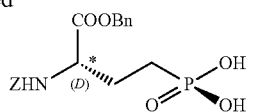

Under ice-cooling, thionyl chloride (2.45 g, 20.6 mmol) was added dropwise to benzyl alcohol (27 mL), and the mixture was, while being kept to 5° C. or lower, combined with the prepared D-2-(benzyloxycarbonyl)amino-4-phosphonobutanoic acid (2.50 g, 7.88 mmol). This reaction mixture was continuously stirred at room temperature until the starting material disappeared. The disappearance of the starting material was checked using TLC (eluent: n-butanol/methanol/water=5/2/2 (v/v), detection: UV).

After the reaction, excess benzyl alcohol was distilled off under reduced pressure, the residue was dissolved in ethyl acetate, and washed with saturated brine.

The ethyl acetate layer was liquid-liquid separated, dried over anhydrous magnesium sulfate, concentrated in vacuo at 40° C., the residue was combined with diethyl ether (40 mL), and stirred for one hour or longer. Precipitated crystals were collected by filtration, dried in vacuo at 40° C. and yielded benzyl D-2-benzyloxycarbonylamino-4-phosphonobutanoate (3.00 g, in a yield of 93%).

$[\alpha]_D^{25}$ +15.8 (c=1, MeOH)

IR (cm$^{-1}$): 2324, 3200-2500 (br), 3033, 2951, 2894, 1734, 1679, 1524, 1347, 1186, 1052, 997, 981, 940, 749, 696.

[Chem. 39]

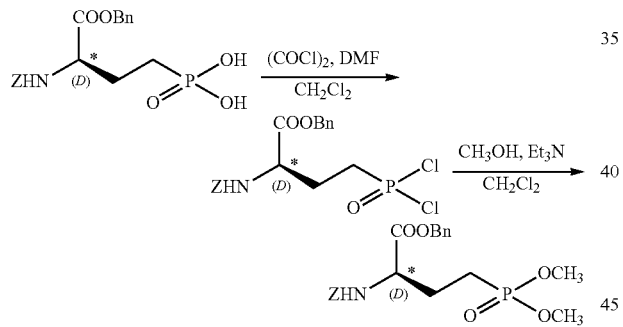

The prepared benzyl D-2-benzyloxycarbonylamino-4-phosphonobutanoate (2.80 g, 6.87 mmol) was suspended in dichloromethane (20 mL), combined with a catalytic amount of dimethylformamide, and further combined with oxalyl dichloride (2.00 g, 15.8 mmol) added dropwise thereto. After being stirred at room temperature for a while, the reaction mixture was concentrated in vacuo, and yielded a yellow oily substance. This was dissolved in dichloromethane (25 mL), combined under ice-cooling with methanol (0.50 g, 15.6 mmol), and further combined with triethylamine (1.45 g, 14.3 mmol) added dropwise, followed by stirring at room temperature overnight. The reaction mixture was combined with silica gel (17 g), concentrated in vacuo, combined with ethyl acetate (300 ml), and stirred thoroughly. This was filtered, the filtrate was concentrated and dried in vacuo at 40° C., and yielded oily benzyl D-2-benzyloxycarbonylamino-4-(dimethoxyphosphoryl)butanoate (2.55 g, in a yield of 85%).

$[\alpha]_D^{25}$ +19.8 (c=$^1$, MeOH), 99.7% ee (column: CHIRAL-PAK IB (5 μm, 4.6 mm in diameter by 250 mm); mobile phase: n-hexane/ethanol=95/5 (v/v); flow rate: 1.0 mL/min; temperature: 25° C.; detection wavelength: UV 220 nm)

IR (cm$^{-1}$): 3245, 3063, 3033, 2953, 2851, 1716, 1536, 1498, 1454, 1242, 1213, 1173, 1025, 815, 737, 696.

[Chem. 40]

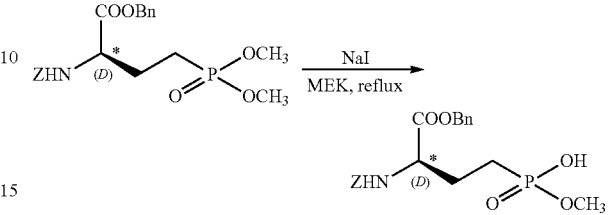

The prepared benzyl D-2-benzyloxycarbonylamino-4-(dimethoxyphosphoryl)butanoate (2.40 g, 5.51 mmol) was dissolved in methyl ethyl ketone (60 mL), combined with sodium iodide (1.40 g, 9.34 mmol), and the mixture was refluxed for 7 hours. After checking that the starting material almost disappeared using TlC (eluent: chloroform/methanol/acetic acid=85/15/3 (v/v), detection: UV), the reaction mixture was concentrated in vacuo and combined with and dissolved in water (60 mL). The resulting aqueous solution was combined with 6 N hydrochloric acid to be acidic, a precipitated yellowish-brown oily substance was extracted with dichloromethane, dried over anhydrous magnesium sulfate, concentrated and dried in vacuo at 40° C. to remove the solvent, and yielded, as a brown solid, benzyl D-2-benzyloxycarbonylamino-4-(hydroxymethoxyphosphoryl)butanoate (2.32 g, in quantitative yield).

$[\alpha]_D^{25}$ +17.5 (c=1, MeOH)

IR (cm$^{-1}$): 3314, 3290, 3058, 3033, 2968, 2955, 2896, 1726, 1698, 1679, 1538, 1269, 1228, 1202, 1148, 1039, 965, 820, 753, 697.

[Chem. 41]

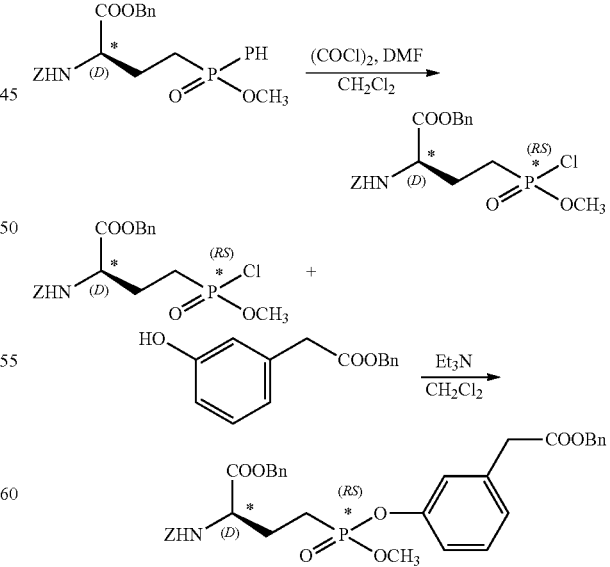

The prepared benzyl D-2-benzyloxycarbonylamino-4-(hydroxymethoxyphosphoryl)butanoate (2.10 g, 4.98 mmol) was dissolved in dichloromethane (20 ml), combined with a catalytic amount of dimethylformamide, combined with oxalyl dichloride (0.74 g, 5.83 mmol) added dropwise, and the mixture was stirred at room temperature for 4 hours. The reaction mixture was concentrated in vacuo, the resulting brown oily substance was dissolved in dichloromethane (20 mL), combined with benzyl 3-hydroxyphenylacetate (1.15 g, 4.75 mmol), and ice-cooled. This was combined with triethylamine (0.58 g, 5.73 mmol) added dropwise and further stirred at room temperature overnight. The reaction mixture was combined with silica gel (10 g), concentrated in vacuo, the residue was subjected to silica gel column chromatography (hexane/ethyl acetate=4/1 to 1/3 (v/v)), and yielded yellow oily benzyl D-2-benzyloxycarbonylamino-4-[(RSp)-(3-benzyloxycarbonylmethylphenoxy)(methoxy)phosphoryl]butanoate (2.9 g, in a yield of 78%).

$[\alpha]_D^{25}$ +10.6 (c=1, MeOH), 99.23 ee (column: CHIRALPAK IB (5 μm, 4.6 mm in diameter by 250 mm); mobile phase: n-hexane/ethanol=95/5 (v/v); flow rate: 1.0 ms/min; temperature: 25° C.; detection wavelength: UV 220 nm)

IR (cm$^{-1}$): 3267, 3063, 3033, 2954, 2852, 1953, 1875, 1721, 1239, 1143, 1041, 1005, 972, 856, 736, 696.

[Chem. 42]

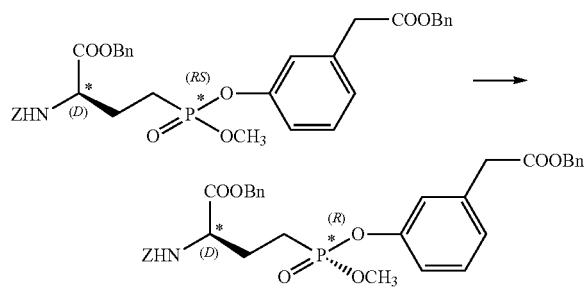

The prepared benzyl D-2-benzyloxycarbonylamino-4-[(RSp)-(3-benzyloxycarbonylmethylphenoxy)(methoxy)phosphoryl]butanoate (1.45 g) was dissolved in ethyl acetate (23.3 mL) and combined with heptane (43.0 mL) gradually added thereto. The resulting solution was seeded with a small amount of crystals of benzyl D-2-benzyloxycarbonylamino-4-[(Rp)-(3-benzyloxycarbonylmethylphenoxy)(methoxy)phosphoryl]butanoate, and stirred at room temperature for 2 hours. After being left stand in a refrigerator overnight, the mixture was further combined with heptane (14.5 mL) and stirred at room temperature for 4 hours. Thereafter this operation was repeated for 7 days, the resulting mixture was further combined with heptane (7.0 mL), stirred at room temperature for 4 hours, precipitated crystals were filtered, washed, dried in vacuo at 40° C., and yielded colorless, powdery benzyl D-2-benzyloxycarbonylamino-4-[(Rp)-(3-benzyloxycarbonylmethylphenoxy)(methoxy)phosphoryl]butanoate (0.32 g, in a yield of 22%).

$[\alpha]_D^{25}$ +18.2 (c=1, MeOH), 93.3% de (column: CHIRALPAK IB (5 μm, 4.6 mm in diameter by 250 mm); mobile phase n-hexane/ethanol=95/5 (v/v); flow rate: 1.0 L/min; temperature: 25° C.; detection wavelength: UV 260 nm)

The prepared benzyl D-2-benzyloxycarbonylamino-4-[(Rp)-(3-benzyloxycarbonylmethylphenoxy)(methoxy)phosphoryl]butanoate (0.32 g) was dissolved in ethyl acetate (10 mL), combined with heptane (27.7 mL) gradually added thereto, and stirred at room temperature overnight. After being left stand in a refrigerator overnight, the mixture was further combined with heptane (5 ml) and stirred at room temperature for 4 hours. Precipitated crystals were filtered, washed, dried in vacuo at 40° C., and yielded colorless, powdery benzyl D-2-benzyloxycarbonylamino-4-[(Rp)-(3-benzyloxycarbonylmethylphenoxy)(methoxy)phosphoryl]butanoate (0.29 g, in a yield of 91%).

$[\alpha]_D^{25}$ +18.8 (c=1, MeOH), 97.9% de (column: CHIRALPAK IB (5 μm, 4.6 mm is diameter by 250 mm); mobile phase: n-hexane/ethanol=95/5 (v/v); flow rate: 1.0 ml/min; temperature: 25° C.; detection wavelength: UV 260 nm)

IR (cm$^{-1}$): 3277, 3186, 3068, 3037, 2987, 2958, 2921, 2891, 2857, 1744, 1718, 1234, 1151, 1130, 1046, 990, 850, 751, 737, 697, 684.

[Chem. 43]

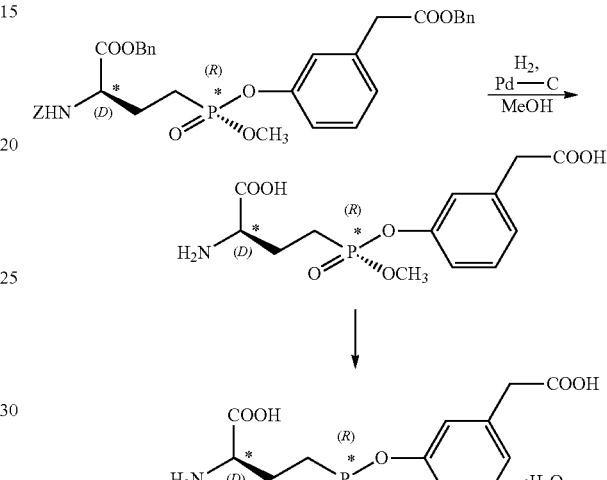

The prepared benzyl D-2-benzyloxycarbonylamino-4-[(Rp)-(3-benzyloxycarbonylmethylphenoxy)(methoxy)phosphoryl]butanoate (220 mg, 0.341 mmol) was dissolved in methanol (10 mL), combined with 10% palladium-carbon (22 mg) while purging the system with nitrogen gas, and the reaction mixture was then stirred at room temperature for 2 hours with blowing hydrogen gas thereinto. After the completion of the reaction, the palladium-carbon was removed by filtration using Celite, the filtrate was concentrated in vacuo, the residue was dissolved in water (10 mL), and washed with toluene (2.5 mL) three times. The aqueous solution was concentrated in vacuo, the residue was combined with ethanol (2 mL), and left stand in a refrigerator overnight. The mixture was subjected to sonication as appropriate, further left stand in a refrigerator overnight, precipitated crystals were filtered, washed, dried in vacuo at 40° C., and yielded, as colorless crystals, D-2-amino-4-[(Rp)-(3-carboxymethylphenoxy)(methoxy)phosphoryl]butanoic acid monohydrate (99 mg, in a yield of 83%). The thermal analysis results of the resulting compound are given in FIG. 6.

Mp (DSC): 108.2° C., $[\alpha]_D^{25}$ +4.4 (c=0.5, H$_2$O), $[\alpha]_D^{25}$ +9.6 (c=0.25, MeOH), 99.9% ee (column: OA-6100 (5 μm, 4.6 mm in diameter by 150 mm); mobile phase: 10% aqueous acetonitrile solution containing 2 mM copper sulfate; flow rate: 1.0 mL/min; temperature: 30° C.; detection wavelength: UV 254 nm)

IR (cm$^{-1}$): 3600-2300 (br), 1683, 1584, 1537, 1485, 1392, 1249, 1145, 1046, 983, 780.

The equal amount mixture obtained in Example 1 was used as a sample and evaluated for glutathione production promotion activity by the following procedure.

Specifically, normal human epidermal cells were inoculated to a 96-well microplate housing a normal human epidermic keratinocyte growth medium (trade name HuMedia KG2, supplied by Kurabo Industries Ltd.) in a cell density of $2.0 \times 10^4$ cells per 96 wells.

Twenty-four (24) hours after the inoculation, the medium was exchanged with a normal human epidermic keratinocyte growth medium (trade name HuMedia KB2, supplied by Kurabo Industries Ltd.) containing the sample in a predetermined concentration, and the cultivation was continued.

As a positive control, a cultivation was performed by a procedure similar to above, except for using, instead of the sample, Nahlsgen (DL-2-amino-4-[(RSp)-(3-carboxymethylphenoxy)(methoxy)phosphoryl]butanoic acid, trade name GGsTop, supplied by Wako Pure Chemical Industries, Ltd.).

As a blank, a cultivation was performed a procedure similar to above, except for not using the sample.

After cultivation for 24 hours, the cells were disrupted by ultrasonication using a phosphoric acid buffer containing 100-μM phenylmethylsulfonyl fluoride, and the total amount of glutathione was quantitatively measured by the aftermentioned glutathione reductase recycling assay.

Specifically, the disrupted cell suspension was combined with reduced nicotinamide adenine dinucleotide phosphate and glutathione reductase, followed by reaction at 37° C. for 10 minutes.

Next, 0.1 M phosphate buffer solution (containing 0.5 M EDTA, pH 7.5) containing 10 mM 5,5'-dithiobis(2-nitrobenzoic acid) was added, the absorbance (at 450 nm) was measured immediately after addition, and after 30 minute-incubation, and the difference between two measurements ((absorbance after 30 minute-incubation)−(absorbance immediately after addition)) was defined as an index for glutathione synthesis quantity.

The total amount of glutathione in the disrupted cell suspension was calculated on the basis of a calibration curve plotted using oxidized glutathione. The protein content in the disrupted cell suspension was quantitatively determined using the Pierce Microplate BCA Protein Assay Kit (Thermo SCIENTIFIC). The glutathione synthesis quantity was evaluated for differences from the untreated specimen (blank) and from the positive control by a significant difference test using Student's t-test. The results are given in the table below.

TABLE 1

| | Conc. | GSH (pmol/μg protein) | | | | Protein (μg/well) | | |
|---|---|---|---|---|---|---|---|---|
| | (μmol/L) | Mean | S.D. | p1 | p2 | Mean | S.D. | p1 |
| Blank (untreated) | 0.00 | 41.0 | ±3.2 | 1.000 | — | 11.8 | ±0.7 | 1.000 |
| Nahlsgen | 10.00 | 44.7 | ±2.7 | 0.129 | 1.000 | 13.9 | ±0.4 | 0.002 |
| Example 1 | 2.00 | 44.2 | ±3.3 | 0.216 | — | 13.1 | ±0.5 | 0.022 |
| Diastereomeric mixture | 10.00 | 48.1 | ±0.7 | 0.005 | 0.052 | 12.6 | ±0.3 | 0.063 |
| | 50.00 | 38.0 | ±7.2 | 0.470 | — | 13.2 | ±0.3 | 0.007 |
| | 250.00 | 41.5 | ±9.6 | 0.926 | — | 13.5 | ±0.6 | 0.008 | p1: Significant difference from blank
p2: Significant difference from Nahlsgen at the same concentration Table 1 demonstrated that, as compared with the blank (untreated cells), the cells treated with the equal amount mixture obtained in Example 1 offered a significantly increased glutathione (GSH) amount as well as or better than the cells treated with Nahlsgen. These results demonstrated that the mixture of a D-GGsTop(R) hydrate and an L-GGsTop(S) hydrate according to the present invention has excellent glutathione production promotion activities as well as or better than Nahlsgen.

The invention claimed is:
1. A method for producing a mixture of a D-2-amino-4-[(Rp)-(3-carboxymethylphenoxy)(methoxy)phosphoryl]butanoic acid hydrate and an L-2-amino-4-[(Sp)-(3-carboxymethylphenoxy)(methoxy)phosphoryl]butanoic acid hydrate, the method comprising subjecting a mixture of four optical isomers represented by Formulae (1-1') to (1-4') to fractional crystallization from water or from a solvent mixture of water and a water-soluble organic solvent, to precipitate a mixture of a D-2-amino-4-[(Rp)-(3-carboxymethylphenoxy)(methoxy)phosphoryl]butanoic acid hydrate represented by Formula (1-1'-1) and an L-2-amino-4-[(Sp)-(3-carboxymethylphenoxy)(methoxy)phosphoryl] butanoic acid hydrate represented by Formula (1-4'-1), Formulae (1-1') to (1-4') and Formulae (1-1'-1) and (1-4'-1) expressed as follows:

[Chem. 1]

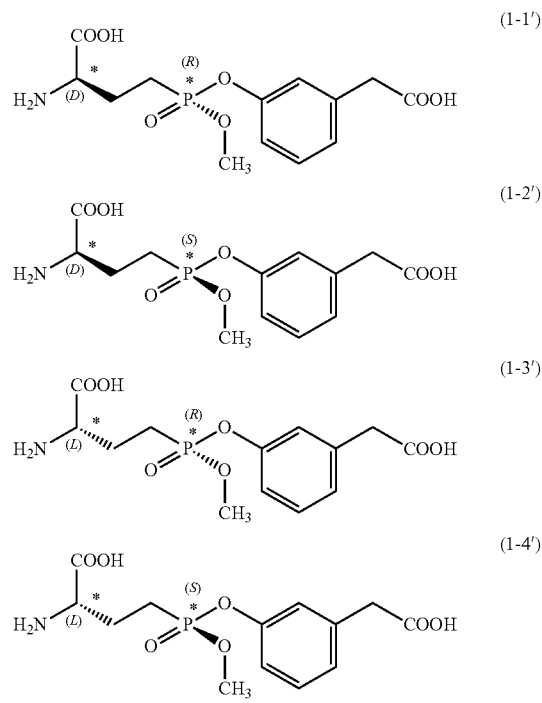

wherein the atoms marked with an asterisk (*) indicate asymmetric atoms,

[Chem. 2]

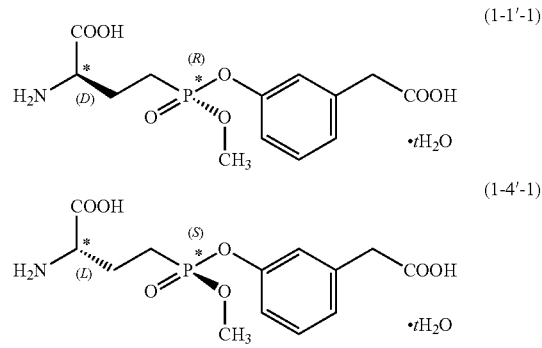

wherein t represents a number greater than 0; and * is as defined above.

2. A mixture of a D-2-amino-4-[(Rp)-(3-carboxymethyl-phenoxy)(methoxy)phosphoryl]butanoic acid hydrate represented by Formula (1-1'-1) and an L-2-amino-4-[(Sp)-(3-carboxymethylphenoxy)(methoxy)phosphoryl]butanoic acid hydrate represented by Formula (1-4'-1), Formulae (1-1'-1) and (1-4'-1) expressed as follows:

[Chem. 3]

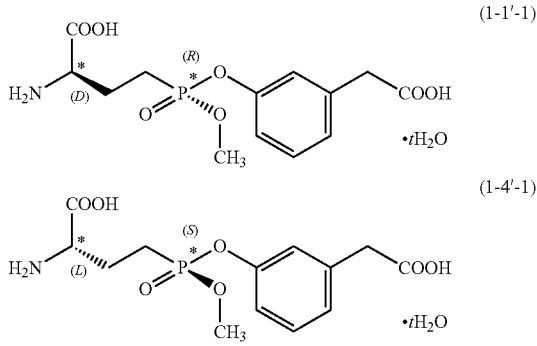

wherein the atoms marked with an asterisk (*) indicate asymmetric atoms; and t represents a number greater than 0.

3. D-2-amino-4-[(Rp)-(3-carboxymethylphenoxy)(methoxy)phosphoryl]butanoic acid hydrate represented by Formula (1-1'-1):

[Chem. 4]

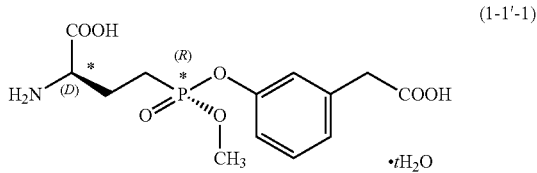

wherein the atoms marked with an asterisk (*) indicate asymmetric atoms; and t represents a number greater than 0.

4. An L-2-amino-4-[(Sp)-(3-carboxymethylphenoxy)(methoxy)phosphoryl]butanoic acid hydrate represented by Formula (1-4'-1):

[Chem. 5]

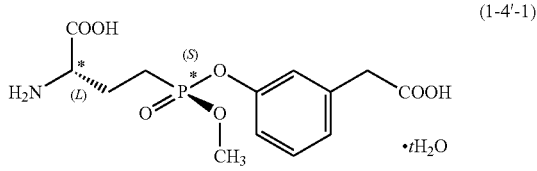

wherein the atoms marked with an asterisk (*) indicate asymmetric atoms; and t represents a number greater than 0.

5. A method for producing a diastereomeric mixture of a D-2-amino-4-[(Rp)-(3-carboxymethylphenoxy)(methoxy)phosphoryl]butanoic acid derivative and a D-2-amino-4-[(Sp)-(3-carboxymethylphenoxy)(methoxy)phosphoryl]butanoic acid derivative, the method comprising esterifying the phosphoric acid moiety of D-2-amino-4-phosphonobutanoic acid represented by Formula (2) to give a diastereomeric mixture, represented by Formula (2-1), of a D-2-amino-4-[(Rp)-(3-carboxymethylphenoxy)(methoxy)phosphoryl]butanoic acid derivative and a D-2-amino-4-[(Sp)-(3-carboxymethylphenoxy)(methoxy)phosphoryl]butanoic acid derivative, Formulae (2) and (2-1) expressed as follows:

[Chem. 6]

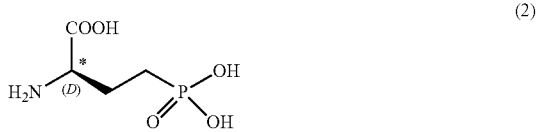

wherein the atom marked with an asterisk (*) indicates an asymmetric atom,

[Chem. 7]

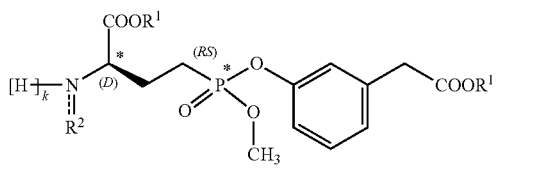

wherein $R^1$ is, identically or differently in each occurrence, selected from hydrogen and a carboxy-protecting group; $R^2$ is selected from benzyloxycarbonyl, phenylmethylidene, and diphenylmethylidene, each being optionally substituted; k represents 0 or 1, where when $R^2$ is optionally substituted benzyloxycarbonyl, k is 1 and the bond between the specified nitrogen atom and $R^2$ is a single bond, and when $R^2$ is optionally substituted phenylmethylidene or optionally substituted diphenylmethylidene, k is 0 and the bond between the specified nitrogen atom and $R^2$ is a double bond; and * is as defined above.

6. A diastereomeric mixture of a D-2-amino-4-[(Rp)-(3-carboxymethylphenoxy)(methoxy)phosphoryl]butanoic acid derivative and a D-2-amino-4-[(Sp)-(3-carboxymethylphenoxy)(methoxy)phosphoryl]butanoic acid derivative, the diastereomeric mixture being represented by Formula (2-1):

[Chem. 8]

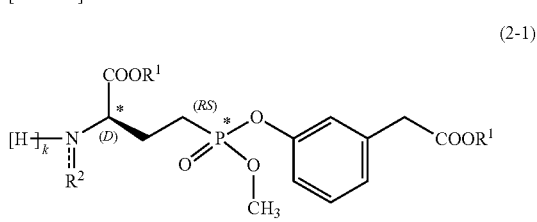

wherein $R^1$ is, identically or differently in each occurrence, selected from hydrogen and a carboxy-protecting group; $R^2$ is selected from benzyloxycarbonyl, phenylmethylidene, and diphenylmethylidene, each being optionally substituted; k represents 0 or 1, where when $R^2$ is optionally substituted benzyloxycarbonyl, k is 1 and the bond between the specified nitrogen atom and $R^2$ is a single bond, and when $R^2$ is optionally substituted phenylmethylidene or optionally substituted diphenylmethylidene, k is 0 and the bond between the specified nitrogen atom and $R^2$ is a double bond; and the atoms marked with an asterisk (*) indicate asymmetric atoms.

7. A method for optically resolving a diastereomeric mixture of a D-2-amino-4-[(Rp)-(3-carboxymethylphenoxy)(methoxy)phosphoryl]butanoic acid derivative and a D-2-amino-4-[(Sp)-(3-carboxymethylphenoxy)(methoxy)phosphoryl]butanoic acid derivative, the method comprising subjecting a diastereomeric mixture, represented by Formula (2-1), of a D-2-amino-4-[(Rp)-(3-carboxymethylphenoxy)(methoxy)phosphoryl]butanoic acid derivative and a D-2-amino-4-[(Sp)-(3-carboxymethylphenoxy)(methoxy)phosphoryl]butanoic acid derivative to fractional crystallization, to give one of optical isomers represented by Formulae (1-1) and (1-2), Formulae (2-1), (1-1), and (1-2) expressed as follows:

[Chem. 9]

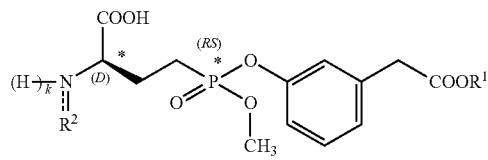

(2-1)

wherein $R^1$ is, identically or differently in each occurrence, selected from hydrogen and a carboxy-protecting group; $R^2$ is selected from benzyloxycarbonyl, phenylmethylidene, and diphenylmethylidene, each being optionally substituted; k represents 0 or 1, where when $R^2$ is optionally substituted benzyloxycarbonyl, k is 1 and the bond between the specified nitrogen atom and $R^2$ is a single bond, and when $R^2$ is optionally substituted phenylmethylidene or optionally substituted diphenylmethylidene, k is 0 and the bond between the specified nitrogen atom and $R^2$ is a double bond; and the atoms marked with an asterisk (*) indicate asymmetric atoms,

[Chem. 10]

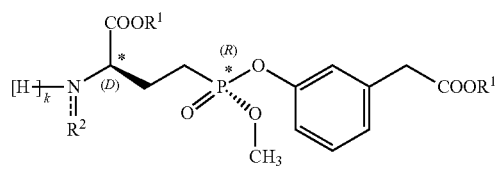

(1-1)

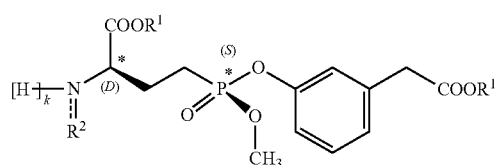

(1-2)

wherein $R^1$, $R^2$, k, and * are as defined above.

8. A method for producing a D-2-amino-4-[(p)-(3 carboxymethylphenoxy)(methoxy)phosphoryl]butanoic acid hydrate, the method comprising:

subjecting a D-2-amino-4-[(Rp)-(3-carboxymethylphenoxy)(methoxy)phosphoryl]butanoic acid derivative represented by Formulae (1-1) to deprotection treatment to give a D-2-amino-4-[(Rp)-(3-carboxymethylphenoxy)(methoxy)phosphoryl]butanoic acid represented by Formula (1-1'); and subjecting the resulting D-2-amino-4-[(Rp)-(3-carboxymethylphenoxy)(methoxy)phosphoryl]butanoic acid to crystallization from water or from a solvent mixture of water and a water-soluble organic solvent, to give a D-2-amino-4-[(Rp)-(3-carboxymethylphenoxy)(methoxy)phosphoryl]butanoic acid hydrate represented by Formula (1-1'-1), Formulae (1-1), (1-1'), and (1-1'-1) expressed as follows:

[Chem. 11]

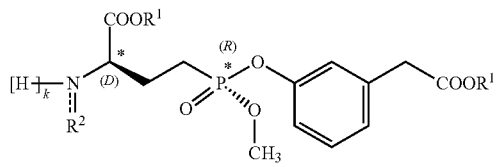

(1-1)

wherein $R^1$ is, identically or differently in each occurrence, selected from hydrogen and a carboxy-protecting group; $R^2$ is selected from benzyloxycarbonyl, phenylmethylidene, and diphenylmethylidene, each being optionally substituted; k represents 0 or 1, where when $R^2$ is optionally substituted benzyloxycarbonyl, k is 1 and the bond between the specified nitrogen atom and $R^2$ is a single bond, and when $R^2$ is optionally substituted phenylmethylidene or optionally substituted diphenylmethylidene, k is 0 and the bond between the specified nitrogen atom and $R^2$ is a double bond; and the atoms marked with an asterisk (*) indicate asymmetric atoms,

[Chem. 12]

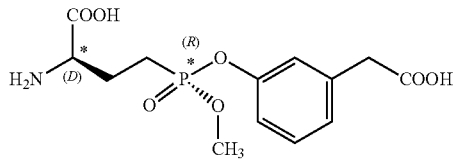

(1-1')

wherein * is as defined above,

[Chem. 13]

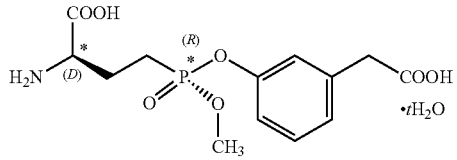

(1-1'-1)

wherein the atoms marked with an asterisk (*) indicate asymmetric atoms; and t represents a number greater than 0.

9. A method for producing a diastereomeric mixture of an L-2-amino-4-[(Rp)-(3)-carboxymethylphenoxy) (methoxy)

phosphoryl]butanoic acid derivative and an L-2-amino-4-[(Sp)-(3-carboxymethylphenoxy)(methoxy)phosphoryl]butanoic acid derivative, the method comprising esterifying the phosphonic acid moiety of L-2-amino-4-phosphonobutanoic acid represented by Formula (3) to give a diastereomeric mixture, represented by Formula (3-1), of an L-2-amino-4-[(Rp)-(3-carboxymethylphenoxy)(methoxy)phosphoryl]butanoic acid derivative and an L-2-amino-4-[(Sp)-(3-carboxymethylphenoxy)(methoxy)phosphoryl]butanoic acid derivative Formulae (3) and (3-1) expressed as follows:

[Chem. 14]

(3)

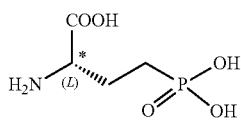

wherein the atom marked with an asterisk (*) indicates an asymmetric atom,

[Chem. 15]

(3-1)

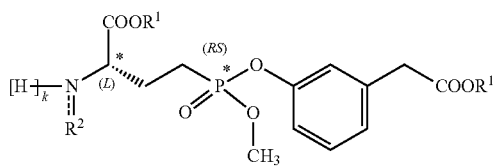

wherein $R^1$ is, identically or differently in each occurrence, selected from hydrogen and a carboxy-protecting group; $R^2$ is selected from benzyloxycarbonyl, phenylmethylidene, and diphenylmethylidene, each being optionally substituted; k represents 0 or 1, where when $R^2$ is optionally substituted benzyloxycarbonyl, k is 1 and the bond between the specified nitrogen atom and R is a single bond, and when $R^2$ is optionally substituted phenylmethylidene or optionally substituted diphenylmethylidene, k is 0 and the bond between the specified nitrogen atom and $R^2$ is a double bond; and * is as defined above.

10. A diastereomeric mixture of an L-2-amino-4-[(Rp)-(3-carboxymethylphenoxy)(methoxy)phosphoryl]butanoic acid derivative and an L-2-amino-4-[(Sp)-(3-carboxymethylphenoxy)(methoxy)phosphoryl]butanoic acid derivative, the diastereomeric mixture being represented by Formula (3-1):

[Chem. 16]

(3-1)

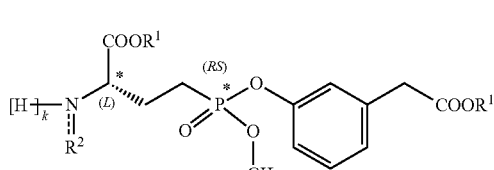

wherein $R^1$ is, identically or differently in each occurrence, selected from hydrogen and a carboxy-protecting group; $R^2$ is selected from benzyloxycarbonyl, phenylmethylidene, and diphenylmethylidene, each being optionally substituted; k represents 0 or 1, where when $R^2$ is optionally substituted benzyloxycarbonyl, k is 1 and the bond between the specified nitrogen atom and $R^2$ is a single bond, and when $R^2$ is optionally substituted phenylmethylidene or optionally substituted diphenylmethylidene, k is 0 and the bond between the specified nitrogen atom and $R^2$ is a double bond; and the atoms marked with an asterisk (*) indicate asymmetric atoms.

11. A method for optically resolving a diastereomeric mixture of an L-2-amino-4-[(Rp)-(3-carboxymethylphenoxy)(methoxy)phosphoryl]butanoic acid derivative and an L-2-amino-4-[(Sp)-(3-carboxymethylphenoxy)(methoxy)phosphoryl]butanoic acid derivative, the method comprising subjecting a diastereomeric mixture, represented by Formula (3-1), of an L-2-amino-4-[(Rp)-(3-carboxymethylphenoxy)(methoxy)phosphoryl]butanoic acid derivative and an L-2-amino-4-[(Sp)-(3-carboxymethylphenoxy)(methoxy)phosphoryl]butanoic acid derivative to fractional crystallization, to give one of optical isomers represented by Formulae (1-3) and (1-4), Formulae (3-1), (1-3), and (1-4) expressed as follows:

[Chem. 17]

(3-1)

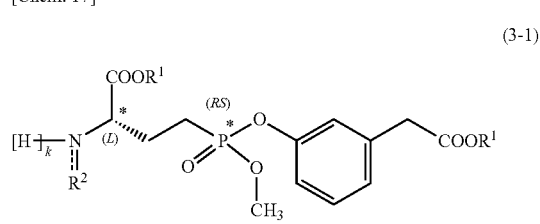

wherein $R^1$ is, identically or differently is each occurrence, selected from hydrogen and a carboxy-protecting group; $R^2$ is selected from benzyloxycarbonyl, phenylmethylidene, and diphenylmethylidene, each being optionally substituted; k represents 0 or 1, where when $R^2$ is optionally substituted benzyloxycarbonyl, k is 1 and the bond between the specified nitrogen atom and $R^2$ is a single bond, and when $R^2$ is optionally substituted phenylmethylidene or optionally substituted diphenylmethylidene, k is 0 and the bond between the specified nitrogen atom and $R^2$ is a double bond; and the atoms marked with an asterisk (*) indicate asymmetric atoms,

[Chem. 15]

(1-3)

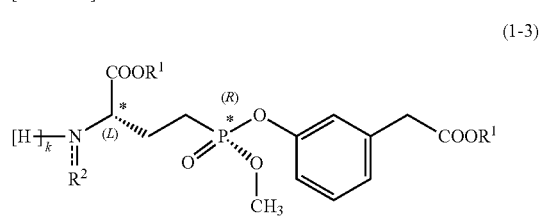

(1-4)

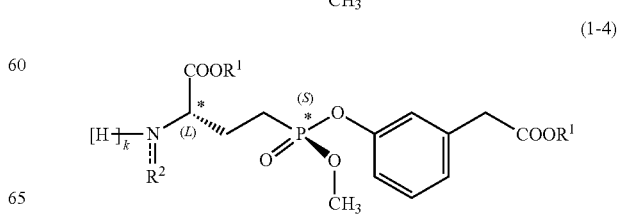

wherein $R^1$, $R^2$, k, and * are as defined above.

12. A method for producing an L-2-amino-4-[(Sp)-(3-carboxymethylphenoxy)(methoxy)phosphoryl]butanoic acid hydrate, the method comprising:

subjecting an L-2-amino-4-[(Sp)-(3-carboxymethylphenoxy)(methoxy)phosphoryl]butanoic acid derivative represented by Formula (1-4) to deprotection treatment to give L-2-amino-4-[(Sp)-(3-carboxymethylphenoxy)(methoxy)phosphoryl]butanoic acid represented by Formula (1-4'); and subjecting the resulting L-2-amino-4-[(Sp)-(3-carboxymethylphenoxy)(methoxy)phosphoryl]butanoic acid to crystallization from water or from a solvent mixture of water and a water-soluble organic solvent, to give an L-2-amino-4-[(Sp)-(3-carboxymethylphenoxy)(methoxy)phosphoryl]butanoic acid hydrate represented by Formula (1-4'-1), Formulae (1-4), (1-4'), and (1-4'-1) expressed as follows:

[Chem. 19]

(1-4)

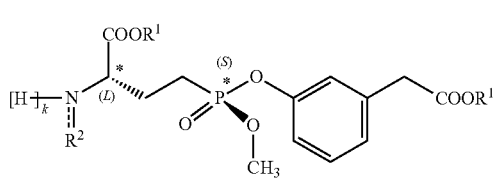

wherein $R^1$ is, identically or differently in each occurrence, selected from hydrogen and a carboxy-protecting group; $R^2$ is selected from benzyloxycarbonyl, phenylmethylidene, and diphenylmethylidene, each being optionally substituted; k represents 0 or 1, where when $R^2$ is optionally substituted benzyloxycarbonyl, k is 1 and the bond between the specified nitrogen atom and $R^2$ is a single bond, and when $R^2$ is optionally substituted phenylmethylidene or optionally substituted diphenylmethylidene, k is 0 and the bond between the specified nitrogen atom and $R^2$ is a double bond; and the atoms marked with an asterisk (*) indicate asymmetric atoms,

[Chem. 20]

(1-4')

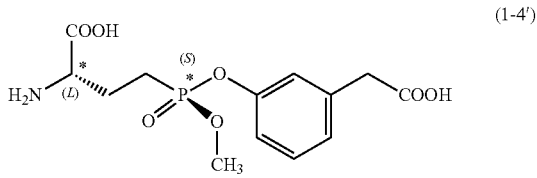

wherein * is as defined above,

[Chem. 21]

(1-4'-1)

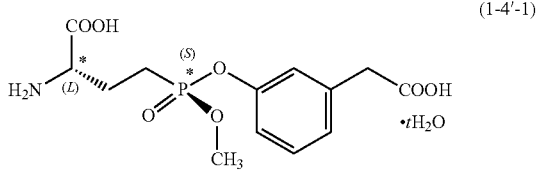

wherein the atoms marked with an asterisk (*) indicate asymmetric atoms; and t represents a number greater than 0.

* * * * *